United States Patent
Lou et al.

(10) Patent No.: US 11,136,583 B2
(45) Date of Patent: Oct. 5, 2021

(54) METHODS AND MATERIALS FOR TREATING CANCER

(71) Applicant: Mayo Foundation for Medical Education and Research, Rochester, MN (US)

(72) Inventors: Zhenkun Lou, Rochester, MN (US); Bo Qin, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 140 days.

(21) Appl. No.: 16/477,049

(22) PCT Filed: Jan. 9, 2018

(86) PCT No.: PCT/US2018/012911
§ 371 (c)(1),
(2) Date: Jul. 10, 2019

(87) PCT Pub. No.: WO2018/132358
PCT Pub. Date: Jul. 19, 2018

(65) Prior Publication Data
US 2019/0330638 A1    Oct. 31, 2019

Related U.S. Application Data

(60) Provisional application No. 62/444,475, filed on Jan. 10, 2017.

(51) Int. Cl.
| | | |
|---|---|---|
| *C12N 15/113* | (2010.01) | |
| *A61K 41/00* | (2020.01) | |
| *A61K 47/69* | (2017.01) | |

(52) U.S. Cl.
CPC ...... *C12N 15/1137* (2013.01); *A61K 41/0038* (2013.01); *A01K 2217/05* (2013.01); *A61K 47/6923* (2017.08); *C12N 2310/14* (2013.01); *C12N 2320/31* (2013.01)

(58) Field of Classification Search
None
See application file for complete search history.

(56) References Cited

U.S. PATENT DOCUMENTS

| | | |
|---|---|---|
| 2004/0110668 A1 | 6/2004 | Burgess et al. |
| 2009/0311702 A1 | 12/2009 | Shak et al. |
| 2012/0302815 A1 | 11/2012 | Chen et al. |

FOREIGN PATENT DOCUMENTS

| | | |
|---|---|---|
| WO | WO 2015/179955 | 12/2015 |
| WO | WO 2016/004387 | 1/2016 |

OTHER PUBLICATIONS

Ayrapetov et al., "DNA double-strand breaks promote methylation of histone H3 on lysine 9 and transient formation of repressive chromatin," Proc. Natl. Acad. Sci. USA, 111(25):9169-74, Jun. 2014.
Brown and Jackson, "Ubiquitylation, neddylation and the DNA damage response," Open Biol., 5(4):150018, Apr. 2015.
Bunting et al., "53BP1 Inhibits Homologous Recombination in Brca1-Deficient Cells by Blocking Resection of DNA Breaks," Cell, 141(2):243-54, Apr. 2010.
Burma et al., "ATM Phosphorylates Histone H2AX in Response to DNA Double-strand Breaks," J. Biol. Chem., 276(45):42462-7, Sep. 2001.
Cai et al., "UFBP1, a Key Component of the Ufm1 Conjugation System, Is Essential for Ufmylation-Mediated Regulation of Erythroid Development," PLoS Genetics, 11(11):e1005643, Nov. 2015.
Celeste et al., "Genomic instability in mice lacking histone H2AX," Science, 296(5569):922-7, May 2002.
Chakraborty et al., "Dynamic phosphorylation of HP1α regulates mitotic progression in human cells," Nat. Commun., 5(1):3445, Mar. 2014.
Chen et al., "BRCA1, BRCA2, and Rad51 Operate in a Common DNA Damage Response Pathway," Cancer Res., 59(7):1752s-6s, Apr. 1999.
Goldberg et al., "MDC1 is required for the intra-S-phase DNA damage checkpoint," Nature 421(6926):952-6, 2003.
Habisov et al., "Structural and Functional Analysis of a Novel Interaction Motif within UFM1-activating Enzyme 5 (UBA5) Required for Binding to Ubiquitin-like Proteins and Ufmylation," J. Biol. Chem., 291(17):9025-41, Jan. 2016.
Harper and Elledge, "The DNA damage response: ten years after," Mol. Cell, 28(5):739-45, Dec. 2007.
Hergovich et al., "NDR kinases regulate essential cell processes from yeast to humans," Nat. Rev. Mol. Cell Biol., 7(4):253-64, Apr. 2006.
Jungmichel et al., "The molecular basis of ATM-dependent dimerization of the Mdc1 DNA damage checkpoint mediator," Nucleic Acids Res., 40(9):3913-28, May 2012.
Kaidi and Jackson, "KAT5 tyrosine phosphorylation couples chromatin sensing to ATM signalling," Nature, 498:70-4, May 2013.
Kang et al., "Two Novel Ubiquitin-fold Modifier 1 (Ufm1)-specific Proteases, UfSP1 and UfSP2," J. Biol. Chem., 282:5256-62, Feb. 2007.
Kim et al., "Linker Histone H1.2 Cooperates with Cul4A and PAF1 to Drive H4K31 Ubiquitylation-Mediated Transactivation," Cell Reports, 5(6):1690-703, Dec. 2013.
Kim et al., "Overexpression of a novel regulator of p120 catenin, NLBP, promotes lung adenocarcinoma proliferation," Cell Cycle, 12(15):2443-536, Aug. 2013.
Kim et al., "Substrate Specificities and Identification of Putative Substrates of ATM Kinase Family Members," J. Biol. Chem., 274(53):37538-43, Dec. 1999.

(Continued)

*Primary Examiner* — Tracy Vivlemore
(74) *Attorney, Agent, or Firm* — Fish & Richardson P.C.

(57) ABSTRACT

This document provides methods and materials involved in treating cancer. For example, methods and materials for using an inhibitor of UFM1 activity or expression and/or an inhibitor of UFL1 activity or expression to reduce a cancer cell's ability to carry out a DDR, thereby increasing the sensitivity of cancer cells to treatment with a DNA damaging therapy such as radiation or chemotherapy, are provided.

16 Claims, 20 Drawing Sheets

Specification includes a Sequence Listing.

(56) References Cited

OTHER PUBLICATIONS

Komatsu et al., "A novel protein-conjugating system for Ufm1, a ubiquitin-fold modifier," Embo J., 23(9):1977-86, May 2004.
Lavin, "Ataxia-telangiectasia: from a rare disorder to a paradigm for cell signalling and cancer," Nat. Rev. Mol. Cell Biol., 9(10):759-69, Oct. 2008.
Lee and Paull, "Direct activation of the ATM protein kinase by the Mre11/Rad50/Nbs1 complex," Science, 304(5667):93-6, Apr. 2004.
Lemaire et al., "Ubiquitin Fold Modifier 1 (UFM1) and Its Target UFBP1 Protect Pancreatic Beta Cells from ER Stress-Induced Apoptosis," PLoS One, 6(4):e18517, Apr. 2011.
Liu et al., "A divergent role of the SIRT1-TopBP1 axis in regulating metabolic checkpoint and DNA damage checkpoint," Mol. Cell, 56(5):681-95, Dec. 2014.
Liu et al., "Structural mechanism of the phosphorylation-dependent dimerization of the MDC1 forkhead-associated domain," Nucleic Acids Res., 40(9):3898-912, Jan. 2012.
Lou et al., "MDC1 is coupled to activated CHK2 in mammalian DNA damage response pathways," Nature, 421(6926):957-61, Feb. 2003.
Morales et al., "The Rad50S allele promotes ATM-dependent DNA damage responses and suppresses ATM deficiency: implications for the Mre11 complex as a DNA damage sensor," Genes Dev., 19:3043-54, 2005.
Moynahan et al., "BRCA2 Is Required for Homology-Directed Repair of Chromosomal Breaks," Mol. Cell, 7(2):263-72, Feb. 2001.
Pang et al., "UFM1 Protects Macrophages from oxLDL-Induced Foam Cell Formation Through a Liver X Receptor [alpha] Dependent Pathway," J. Atheroscler. Thromb., 22(11):1124-40, Jun. 2015.
PCT International Preliminary Report on Patentability in International Appln. No. PCT/US2018/012911 dated Jul. 25, 2019, 8 pages.
PCT International Search Report and Written Opinion in International Appln. No. PCT/US2018/012911 dated Jun. 25, 2018, 12 pages.
Rappold et al., "Tumor suppressor p53 binding protein 1 (53BP1) is involved in DNA damage-signaling pathways," J. Cell Biol., 153(3):613-20, Apr. 2001.
Reinhardt and Yaffe, "Kinases that control the cell cycle in response to DNA damage: Chk1, Chk2, and MK2," Curr. Opin. Cell Biol., 21(2):245-55, Apr. 2009.
Rogakou et al., "DNA Double-stranded Breaks Induce Histone H2AX Phosphorylation on Serine 139," J. Biol. Chem., 273:5858-68, Mar. 1998.
Scully et al., "Dynamic changes of BRCA1 subnuclear location and phosphorylation state are initiated by DNA damage," Cell, 90(3):425-35, Aug. 1997.
Seluanov et al., "DNA end joining becomes less efficient and more error-prone during cellular senescence," Proc. Natl. Acad. Sci. USA, 101(20):7624-9, May 2004.
Shiloh and Ziv,"The ATM protein kinase: regulating the cellular response to genotoxic stress, and more," Nat. Rev. Mol. Cell Biol., 14(4):197-210 Mar. 2013.
Shiwaku et al., "Suppression of the novel ER protein Maxer by mutant ataxin-1 in Bergman glia contributes to non-cell-autonomous toxicity," Embo J., 29(14):2446-60, Jul. 2010.
Stewart et al., "MDC1 is a mediator of the mammalian DNA damage checkpoint," Nature, 421(6926):961-6, Feb. 2003.
Sun et al., "A role for the Tip60 histone acetyltransferase in the acetylation and activation of ATM," Proc. Natl. Acad. Sci. USA, 102(37):13182-7, Sep. 2005.
Sun et al., "Histone H3 methylation links DNA damage detection to activation of the tumour suppressor Tip60," Nat. Cell Biol., 11(11):1376-82, Sep. 2009.
Tatsumi et al., "A Novel Type of E3 Ligase for the Ufm1 Conjugation System," J. Biol. Chem., 285(8):5417-27, Feb. 2010.
Tatsumi et al., "The Ufm1-activating enzyme Uba5 is indispensable for erythroid differentiation in mice," Nat. Commun., 2(1):181, Feb. 2011.
Tefiai et al., "ER stress signaling promotes the survival of cancer "persister cells" tolerant to EGFR tyrosine kinase inhibitors," Cancer Res., 78(4):1044-57, Feb. 2018.
Uziel et al., "Requirement of the MRN complex for ATM activation by DNA damage," Embo J., 22(20):5612-21, Oct. 2003.
Wang et al., "53BP1, a mediator of the DNA damage checkpoint," Science. 298(5597):1435-8, Nov. 2002.
Wei and Zu, "UFMylation: A Unique & Fashionable Modification for Life," Genomics Proteomics Bioinformatics, 14(3):140-6, Jun. 2016.
Wu et al., "MDC1 regulates intra-S-phase checkpoint by targeting NBS1 to DNA double-strand breaks," Proc. Natl. Acad. Sci. USA,105(32):11200-5, Aug. 2008.
Yoo et al., "Modification of ASC1 by UFM1 Is Crucial for Erα Transactivation and Breast Cancer Development," Mol. Cell, 56(2):261-74, Oct. 2014.
Zeitlin et al., "Double-strand DNA breaks recruit the centromeric histone CENP-A," Proc. Natl. Acad. Sci. USA, 106(37):15762-7, Sep. 2009.
Zhang et al., "RCAD/Ufl1, a Ufm1 E3 ligase, is essential for hematopoietic stem cell function and murine hematopoiesis," Cell Death Differ., 22(12):1922-34, May 2015.
Zhang et al., "Transcriptional Regulation of the Ufm1 Conjugation System in Response to Disturbance of the Endoplasmic Reticulum Homeostasis and Inhibition of Vesicle Trafficking," PLoS One, 7(11):e48587, Nov. 2012.

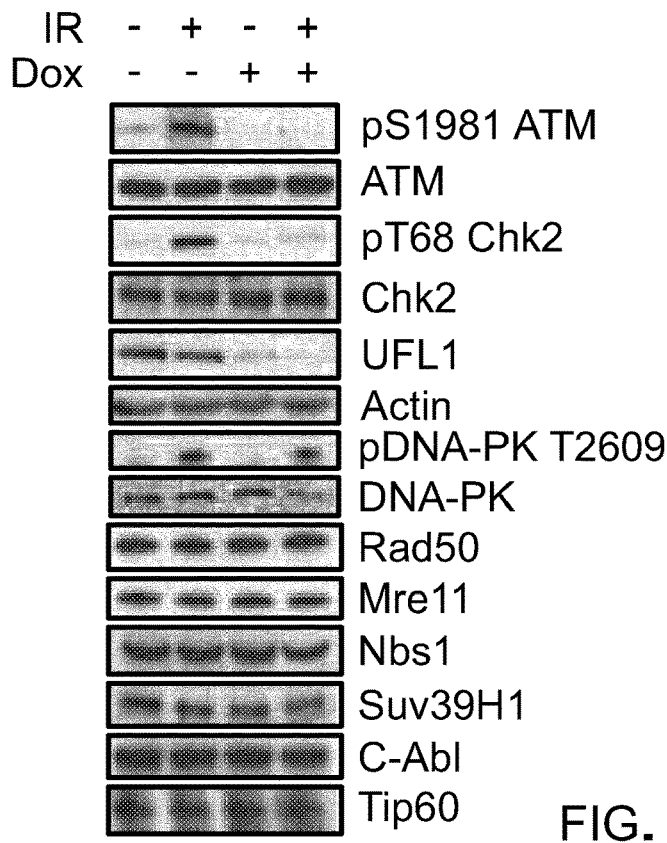
FIG. 1j
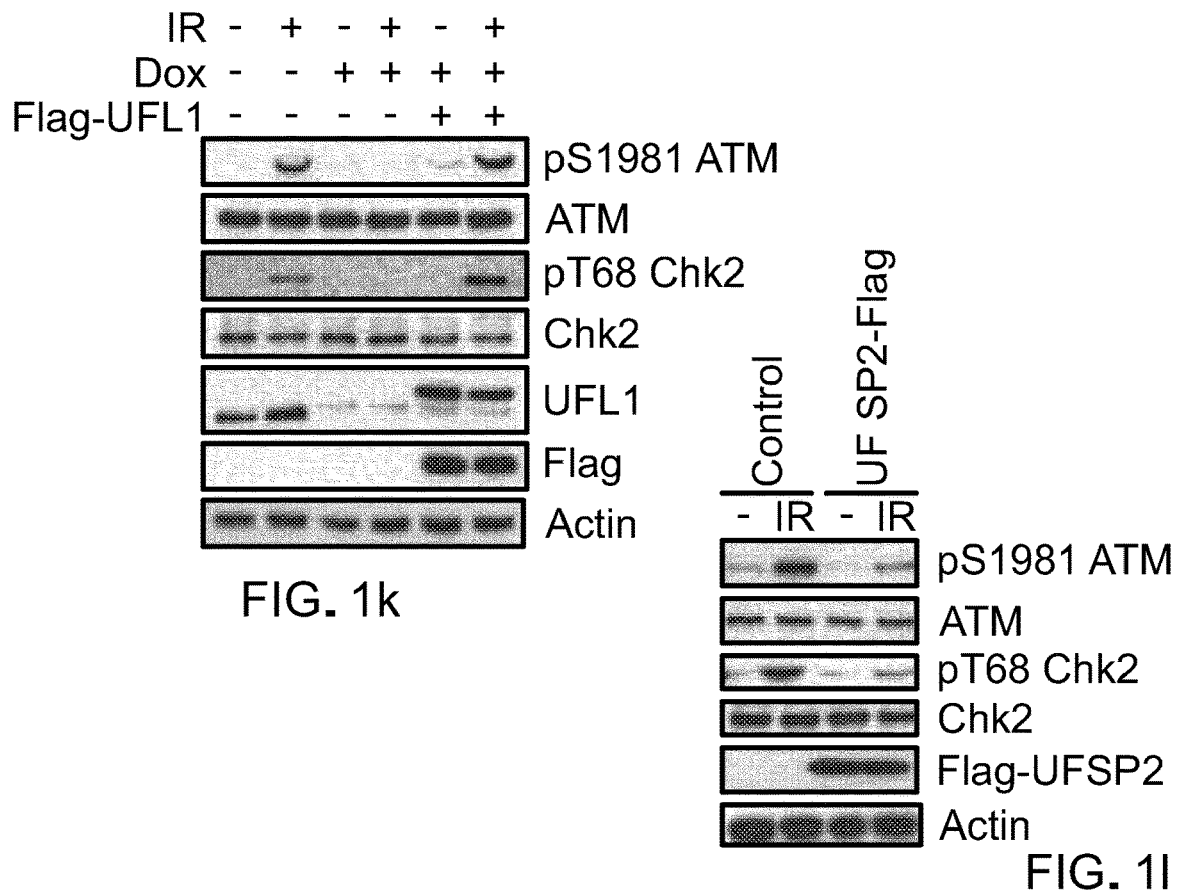
FIG. 1k
FIG. 1l

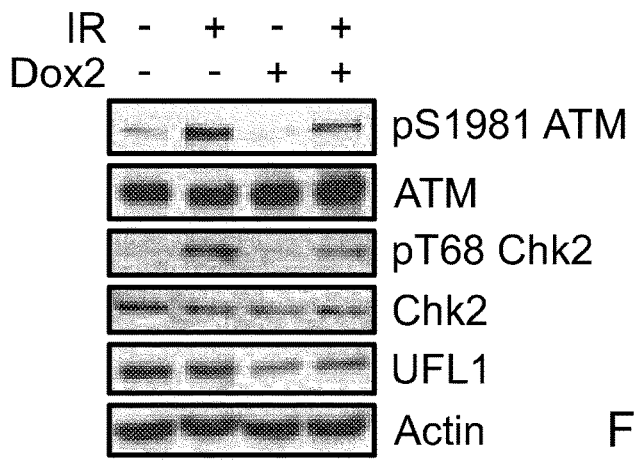
FIG. 2i
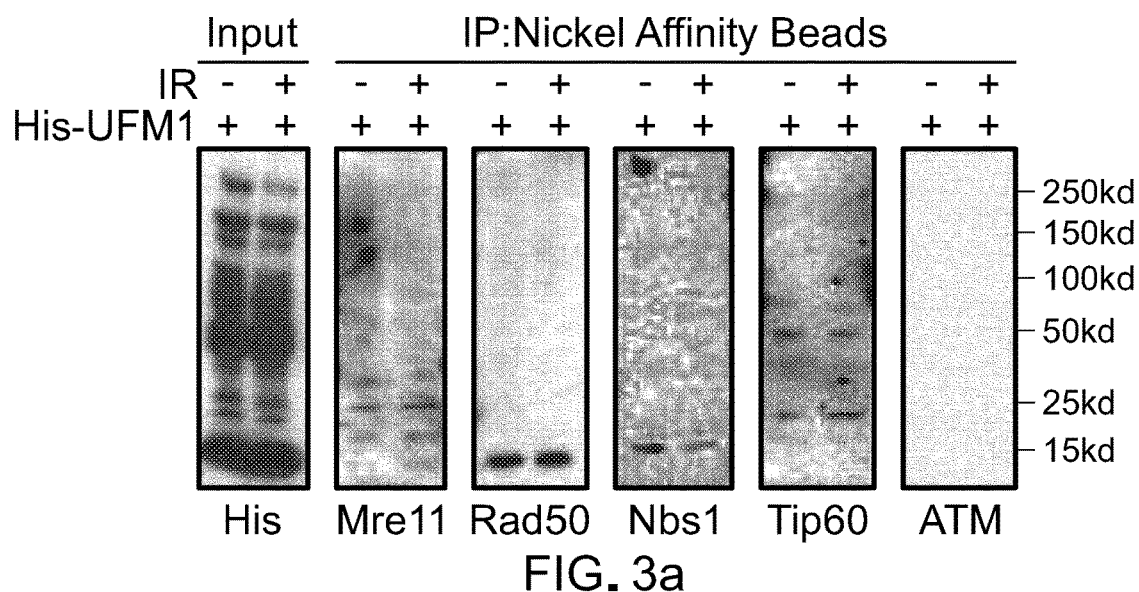
FIG. 3a
FIG. 3b

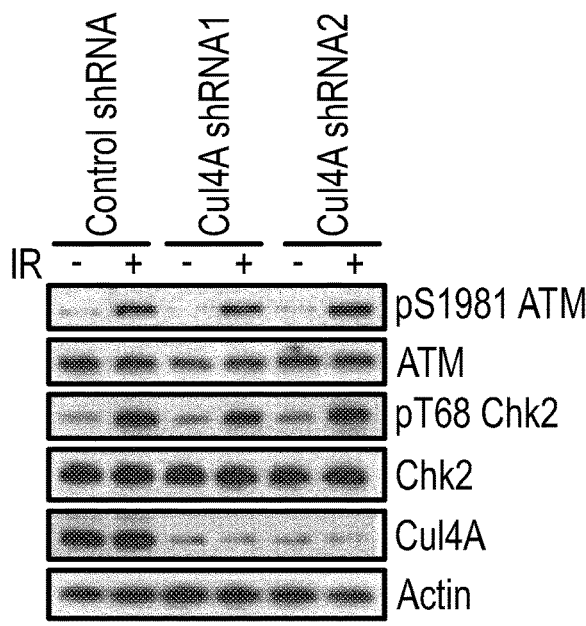
FIG. 3c
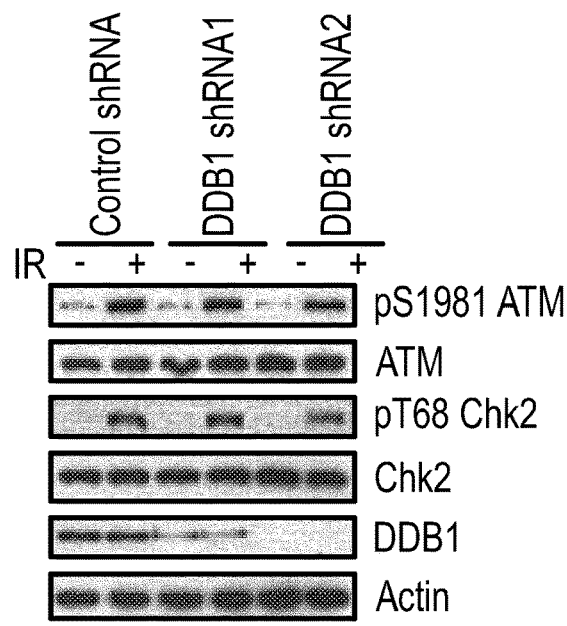
FIG. 3d
UFM1-His Mass Spectrum Data
| Number of Peptides | Protein |
| --- | --- |
| 61 | UFM1 |
| 33 | RPL8 |
| 24 | ZNF281 |
| 20 | H4 |
| 16 | ZIC2 |
| 9 | CAPNS1 |
| 6 | RPS6 |
FIG. 4a
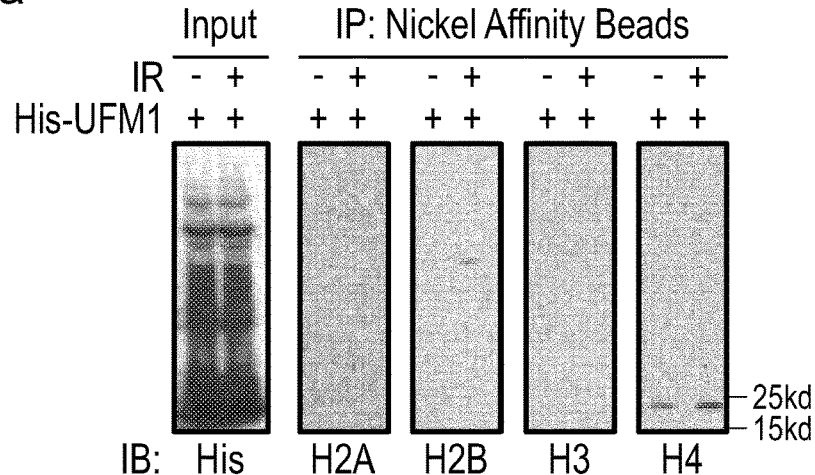
FIG. 4b

| UFM1-H4 Mass Spectrum Data | | Ub-H4 Mass Spectrum Data | |
|---|---|---|---|
| Number of Peptides | Protein | Number of Peptides | Protein |
| 16 | H4 | 163 | H4 |
| 11 | PABPC1 | 80 | UBA52 |
| 13 | STK38 | 69 | UBE2O |
| 10 | VIM | 38 | HSPA5 |
| 7 | RBBP4 | 22 | HNRNPU |
| 4 | HIST3H3 | 19 | VIM |
| 1 | UFM1 | 6 | HIST3H3 |
FIG. 5a
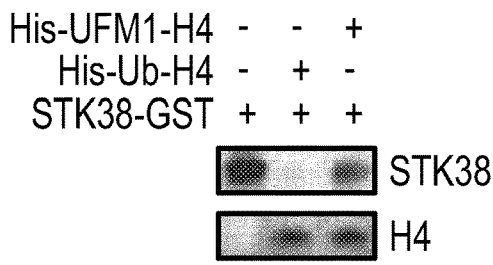
FIG. 5b
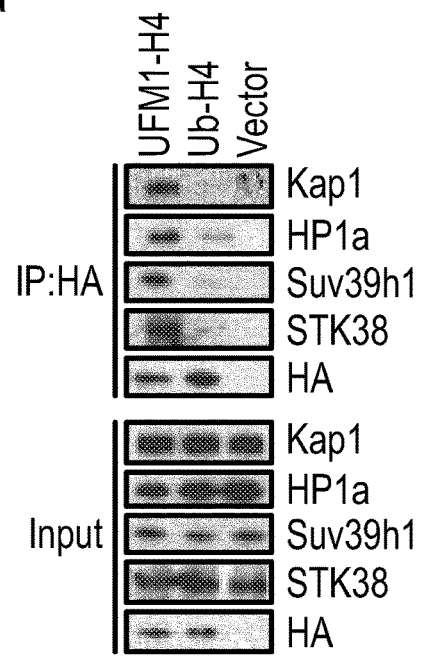
FIG. 5c
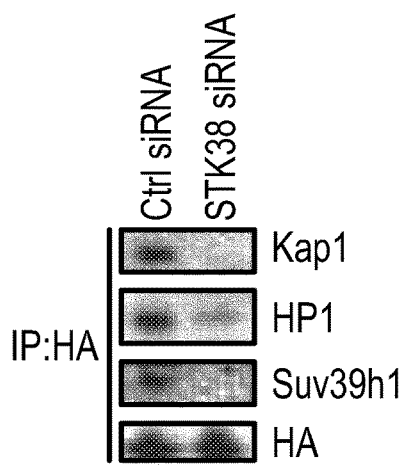
FIG. 5d
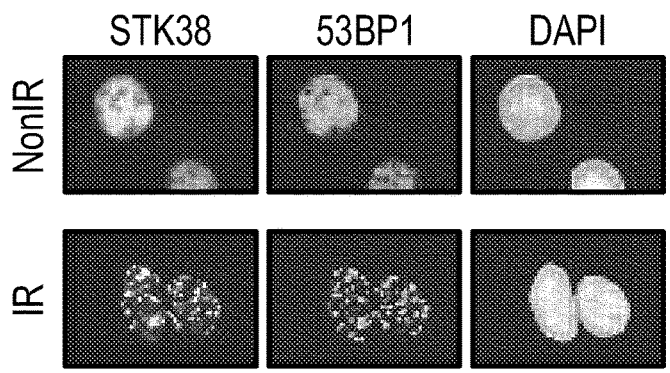
FIG. 5e

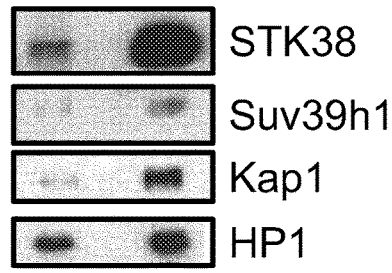
FIG. 6a
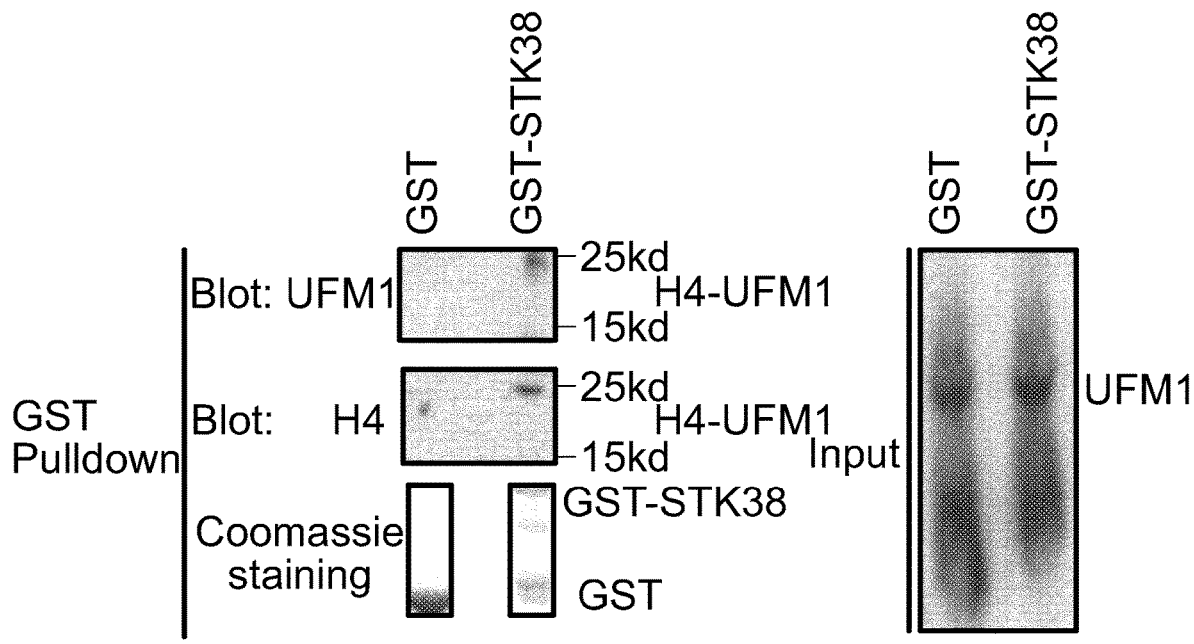
FIG. 6b
| | |
|---|---|
| UBA5 | EDNEWGIELVSE |
| STK38 WT | LCDWWSLGVIMY |
| STK38 2A Mutant | LCDWASAGVIMY |
| STK38 4A Mutant | LCDWASAGAAMY |
FIG. 6c

SEQUENCE LISTING

<160> NUMBER OF SEQ ID NOS: 27

<210> SEQ ID NO 1
<211> LENGTH: 21
<212> TYPE: DNA
<213> ORGANISM: Homo sapiens

<400> SEQUENCE: 1
gaaacacttc tgtgtcagaa a					21

<210> SEQ ID NO 2
<211> LENGTH: 21
<212> TYPE: DNA
<213> ORGANISM: Homo sapiens

<400> SEQUENCE: 2
gctctggaac atgggttgat a					21

<210> SEQ ID NO 3
<211> LENGTH: 21
<212> TYPE: DNA
<213> ORGANISM: Homo sapiens

<400> SEQUENCE: 3
gcagaactga tcgcaaagca t					21

<210> SEQ ID NO 4
<211> LENGTH: 21
<212> TYPE: DNA
<213> ORGANISM: Homo sapiens

<400> SEQUENCE: 4
ggacaagaag atgttactaa a					21

<210> SEQ ID NO 5
<211> LENGTH: 21
<212> TYPE: DNA
<213> ORGANISM: Homo sapiens

<400> SEQUENCE: 5
cgaccgtaag aaggtgactt t					21

<210> SEQ ID NO 6
<211> LENGTH: 21
<212> TYPE: DNA
<213> ORGANISM: Homo sapiens

<400> SEQUENCE: 6
ccttgattgg tgttgccagt t					21

<210> SEQ ID NO 7
<211> LENGTH: 18
<212> TYPE: RNA
<213> ORGANISM: Artificial Sequence
<220> FEATURE:
<223> OTHER INFORMATION: siRNA targeting STK38

<400> SEQUENCE: 7
cgucggccau aaacagcu					18

<210> SEQ ID NO 8
<211> LENGTH: 21
<212> TYPE: RNA
<213> ORGANISM: Artificial Sequence

```
<220> FEATURE:
<223> OTHER INFORMATION: siRNA targeting STK38

<400> SEQUENCE: 8
gccugcaacu uaggcggauu g                                              21

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 9
tacagctcct gggcaacgtg                                                20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 10
tcctgctcct gggcttctcg                                                20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 11
cagtcaagca atggaagaag                                                20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 12
cccgtgccac ccctcagtga                                                20

<210> SEQ ID NO 13
<211> LENGTH: 9
<212> TYPE: PRT
<213> ORGANISM: Homo sapiens

<400> SEQUENCE: 13

Trp Trp Ser Leu Gly Val Ile Met Tyr
1               5

<210> SEQ ID NO 14
<211> LENGTH: 21
<212> TYPE: DNA
<213> ORGANISM: Homo sapiens

<400> SEQUENCE: 14
ctgcggatta ttcctagaga t                                              21

<210> SEQ ID NO 15
<211> LENGTH: 21
```

```
<212> TYPE: DNA
<213> ORGANISM: Homo sapiens

<400> SEQUENCE: 15
gcagtcttaa agtttgcagc a                                              21

<210> SEQ ID NO 16
<211> LENGTH: 21
<212> TYPE: DNA
<213> ORGANISM: Homo sapiens

<400> SEQUENCE: 16
ccaatgatgg aataggaata a                                              21

<210> SEQ ID NO 17
<211> LENGTH: 21
<212> TYPE: DNA
<213> ORGANISM: Homo sapiens

<400> SEQUENCE: 17
gtgttcctga aagtacacct t                                              21

<210> SEQ ID NO 18
<211> LENGTH: 19
<212> TYPE: RNA
<213> ORGANISM: Artificial Sequence
<220> FEATURE:
<223> OTHER INFORMATION: siRNA targeting UFM1

<400> SEQUENCE: 18
cggaagugcu gaugaguua                                                 19

<210> SEQ ID NO 19
<211> LENGTH: 19
<212> TYPE: RNA
<213> ORGANISM: Artificial Sequence
<220> FEATURE:
<223> OTHER INFORMATION: siRNA targeting UFM1

<400> SEQUENCE: 19
gaggaaagca acagaggaa                                                 19

<210> SEQ ID NO 20
<211> LENGTH: 19
<212> TYPE: RNA
<213> ORGANISM: Artificial Sequence
<220> FEATURE:
<223> OTHER INFORMATION: siRNA targeting UFM1

<400> SEQUENCE: 20
caaaugaaca gcaggauua                                                 19

<210> SEQ ID NO 21
<211> LENGTH: 19
<212> TYPE: RNA
<213> ORGANISM: Artificial Sequence
<220> FEATURE:
<223> OTHER INFORMATION: siRNA targeting UFM1

<400> SEQUENCE: 21
gggagaacug aaagggaaa                                                 19

<210> SEQ ID NO 22
<211> LENGTH: 21
<212> TYPE: DNA
```

```
<213> ORGANISM: Homo sapiens

<400> SEQUENCE: 22
ccagtaagca taagtcatat t                                              21

<210> SEQ ID NO 23
<211> LENGTH: 21
<212> TYPE: DNA
<213> ORGANISM: Homo sapiens

<400> SEQUENCE: 23
gagagagaac acatgcaatt t                                              21

<210> SEQ ID NO 24
<211> LENGTH: 21
<212> TYPE: RNA
<213> ORGANISM: Artificial Sequence
<220> FEATURE:
<223> OTHER INFORMATION: siRNA targeting UFL1

<400> SEQUENCE: 24
cagaagaggu caaugauaau u                                              21

<210> SEQ ID NO 25
<211> LENGTH: 21
<212> TYPE: RNA
<213> ORGANISM: Artificial Sequence
<220> FEATURE:
<223> OTHER INFORMATION: siRNA targeting UFL1

<400> SEQUENCE: 25
ucauaugggc aaagggaaau u                                              21

<210> SEQ ID NO 26
<211> LENGTH: 19
<212> TYPE: RNA
<213> ORGANISM: Artificial Sequence
<220> FEATURE:
<223> OTHER INFORMATION: siRNA targeting UFL1

<400> SEQUENCE: 26
cagaagaggu caaugauaa                                                 19

<210> SEQ ID NO 27
<211> LENGTH: 19
<212> TYPE: RNA
<213> ORGANISM: Artificial Sequence
<220> FEATURE:
<223> OTHER INFORMATION: siRNA targeting UFL1

<400> SEQUENCE: 27
ucauaugggc aaagggaaa                                                 19
```

METHODS AND MATERIALS FOR TREATING CANCER

CROSS-REFERENCE TO RELATED APPLICATIONS

This application is a National Stage application under 35 U.S.C. § 371 of International Application No. PCT/US2018/012911, having an International Filing Date of Jan. 9, 2018, which claims the benefit of U.S. Patent Application Ser. No. 62/444,475, filed on Jan. 10, 2017. The disclosures of the prior applications are considered part of (and are incorporated by reference in) the disclosure of this application.

SEQUENCE LISTING

This document includes a sequence listing submitted to the United States Patent and Trademark Office via the electronic filing system as an ASCII text file. The sequence listing, which is incorporated-by-reference herein, is titled "SEQ_ST25.txt," was created on Jan. 4, 2018, and has a size of 5 kilobytes.

BACKGROUND

1. Technical Field

This document relates to methods and materials involved in treating cancer. For example, this document provides methods and materials for using an inhibitor of Ubiquitin Fold Modifier 1 (UFM1) activity or expression and/or an inhibitor of UFM1 specific ligase 1 (UFL1; an ufmylation E3 ligase) activity or expression to reduce a cancer cell's ability to carry out a DNA damage response (DDR), thereby increasing the sensitivity of cancer cells to treatment with a DNA damaging therapy such as radiation or chemotherapy.

2. Background Information

When DNA damage occurs, rapid DNA damage response (DDR) and DNA repair are required to preserve genome integrity. The protein kinase ataxia-telangiectasia mutated (ATM) functions as an apical activator for the whole process, and controls signaling and the DNA repair network. The Mre11-Rad50-Nbs1 (MRN) complex is involved in activation of ATM kinase. Activated ATM phosphorylates histone H2AX at Ser139 (γH2AX) close to DNA damage sites, and γH2AX then recruits MDC1, which serves as a platform for binding more MRN complexes and other DNA repair proteins to amplify DDR signaling and promote DNA repair. In addition, ATM activation is also dependent on the acetyltransferase Tip60. Tip60 is recruited to the sites of DNA damage by binding to H3K9Me3, and in turn acetylates ATM at lysine 3016 and boosts ATM activation. Tip60 itself is phosphorylated by c-Abl, which increases Tip60 activity and reinforces ATM activity. However, early chromatin environment leading to full ATM activation remains unclear.

SUMMARY

This document provides methods and materials involved in treating cancer. For example, this document provides methods and materials for using an inhibitor of UFM1 activity or expression and/or an inhibitor of UFL1 activity or expression to reduce a cancer cell's ability to carry out a DDR, thereby increasing the sensitivity of cancer cells to treatment with a DNA damaging therapy such as radiation or chemotherapy.

As described herein, UFL1, an ufmylation E3 ligase, is involved in ATM activation. UFL1 is recruited to double strand breaks by the Mre11/Rad50/Nbs1 complex, and monoufmylates histone H4 following DNA damage. Monoufmylated histone H4 is recognized by serine/threonine kinase 38 (STK38), which forms a complex with Suv39h1 and promotes H3K9me3 modification, Tip60 recruitment, and ATM signaling. Furthermore, ATM phosphorylates UFL1 at Serine 462, enhancing UFL1 E3 ligase activity and promoting ATM activation in a positive feedback loop. These findings reveal that ufmylation of histone H4 by UFL1 is a step for ATM activation and maintenance of genomic integrity.

Also as described herein, an inhibitor of UFM1 activity or expression and/or an inhibitor of UFL1 activity or expression can be administered to a mammal (e.g., a human) to increase the sensitivity of the mammal's cancer cells to treatment with a DNA damaging therapy such as radiation or chemotherapy. After the sensitivity of the mammal's cancer cells to DNA damaging therapy is increased, a DNA damaging therapy (e.g., radiation or chemotherapy) can be administered to the mammal to reduce the number of cancer cells within the mammal. In some cases, an inhibitor of UFM1 activity or expression and/or an inhibitor of UFL1 activity or expression can be administered together as a combination with a DNA damaging therapy (e.g., radiation or chemotherapy) to reduce the number of cancer cells within the mammal. In some cases, an inhibitor of UFM1 activity or expression and/or an inhibitor of UFL1 activity or expression can be administered within the same week (or within the same day) with a DNA damaging therapy (e.g., radiation or chemotherapy) to reduce the number of cancer cells within the mammal.

In some cases, the number of cancer cells within a mammal treated with both (a) an inhibitor of UFM1 activity or expression and/or an inhibitor of UFL1 activity or expression and (b) a DNA damaging therapy (e.g., radiation or chemotherapy) can be reduced to a level that is more than the level of reduction observed in comparable mammals treated with the inhibitor of UFM1 activity or expression alone, the inhibitor of UFL1 activity or expression alone, or the DNA damaging therapy alone.

This document also provides methods and materials for identifying mammals (e.g., humans) having cancer (e.g., prostate cancer) that is susceptible to treatment with a DNA damaging therapy (e.g., radiation or chemotherapy). For example, cancer cells obtained from a mammal can be assessed for the presence of a reduced level of UFM1 and/or UFL1 polypeptide expression. Those mammals with cancer cells having a reduced level of UFM1 and/or UFL1 polypeptide expression can be classified as being susceptible to treatment with a DNA damaging therapy (e.g., radiation or chemotherapy).

In some cases, a mammal (e.g., a human) having cancer can be treated by (a) detecting the presence of a reduced level of UFM1 and/or UFL1 polypeptide expression in the cancer cells, and (b) administering a DNA damaging therapy (e.g., radiation or chemotherapy) to the mammal.

In general, one aspect of this document features a method for treating cancer in a mammal. The method includes, or consists essentially of, administering an inhibitor of UFM1 activity or expression or an inhibitor of UFL1 activity or expression to the mammal, and administering a DNA damaging therapy to the mammal, where the number of cancer cells within the mammal is reduced to a greater level than the level observed in a comparable mammal administered the DNA damaging therapy in the absence of administration of the inhibitor of UFM1 activity or expression and the inhibitor of UFL1 activity or expression. The mammal can be a human. The cancer can be prostate cancer. The cancer can be breast cancer. The cancer can be resistant to radiation when administered as the sole cancer therapy. In cases where the method includes administering an inhibitor of UFM1 activity or expression to the mammal, and the inhibitor of UFM1 activity or expression can be an siRNA targeting UFM1. In cases where the method includes administering an inhibitor of UFL1 activity or expression to said mammal, the inhibitor of UFL1 activity or expression can be an siRNA targeting UFL1. The DNA damaging therapy can be radiation therapy.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 3. UFL1 monoufmylates histone H4 and promotes ATM activation. a, His-ufmylated proteins were purified from untreated or irradiated 293T cells and detected with the indicated antibodies. b, In vitro ufmylation assay. Purified UBA5, UFC1, UFL1, UFM1, UFBP1 and H2A, H2B, H3 or H4 proteins were mixed together in the presence of ATP and $MgCl_2$ at 30° C. for 90 min. c-d, ATM signaling in cells expressing Cul4A shRNA or DDB1 shRNA after IR (10 Gy, 1 hr).

DETAILED DESCRIPTION

Figure 1A:
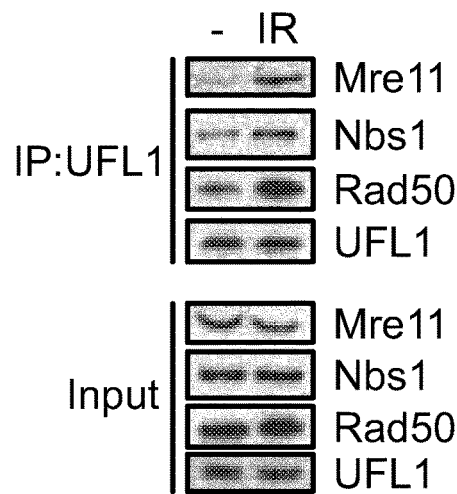
FIG. 1. UFL1 protein accumulates at DSBs through the MRN complex and regulates ATM signaling. a, Co-immunoprecipitation of UFL1 and the MRN complex in U2OS cells with or without ionizing radiation (10 Gy). b, Immunofluorescence of UFL1 and γ H2AX in U2OS cells irradiated with IR (2 Gy). c, Immunofluorescence of UFL1 and γ H2AX at a single DSB generated by I-SecI. d-e, Immunofluorescence of UFL1 in Mre11 knockdown cells or NBS1 deficient cells NBST/Nbs1 reconstituted cells. f-g, HeLa cells integrated with HR reporter or transfected with NHEJ reporter were infected with the UFL1 Tet-on shRNA1 virus and subjected to the HR assay (f) or NHEJ assay (g) as described in the method. Data presented as mean±SEM. of three biological triplicates. P<0.01. h, Colony-formation assay following IR was performed with UFL1 Tet-on shRNA cells with or without doxycycline (Dox). The data presented are mean±SEM for three independent experiments. p<0.01. i, Time course of γH2AX foci formation in control or UFL1 knockdown cells. The data presented are mean±SEM for three independent experiments. **p<0.01. j-k, ATM signaling in cells expressing inducible UFL1 shRNA or reconstitution with shRNA resistant Flag-UFL1 1 h after 10 Gy IR. 1, ATM signaling in UFSP2 expressing cells.

This document provides methods and materials for treating cancer. For example, this document provides methods and materials for using an inhibitor of UFM1 activity or expression and/or an inhibitor of UFL1 activity or expression to increase the sensitivity of cancer cells to treatment with a DNA damaging therapy (e.g., radiation or chemotherapy). Once the sensitivity of the mammal's cancer cells to a DNA damaging therapy (e.g., radiation or chemotherapy) is increased, a DNA damaging therapy (e.g., radiation or chemotherapy) can be administered to the mammal to reduce the number of cancer cells within the mammal. In some cases, a mammal having cancer can be treated with both (a) an inhibitor of UFM1 activity or expression and/or an inhibitor of UFL1 activity or expression and (b) a DNA damaging therapy (e.g., radiation or chemotherapy) under conditions wherein the number of cancer cells within a mammal is reduced to a level that is more than the level of reduction observed in comparable mammals treated with an UFM1 inhibitor alone, an UFL1 inhibitor alone, or a DNA damaging therapy alone.

Any type of mammal having cancer can be treated as described herein. For example, humans and other primates such as monkeys having cancer can be treated with one or more inhibitors of UFM1 activity or expression and/or one or more inhibitors of UFL1 activity or expression to increase the sensitivity of cancer cells to treatment with a DNA damaging therapy (e.g., radiation or chemotherapy) together with and/or followed by treatment with a DNA damaging therapy (e.g., radiation or chemotherapy) to reduce the number of cancer cells present within the mammal. In some cases, dogs, cats, horses, cows, pigs, sheep, mice, and rats can be treated with (a) one or more inhibitors of UFM1 activity or expression and/or one or more inhibitors of UFL1 activity or expression together with and/or followed by (b) a DNA damaging therapy (e.g., radiation or chemotherapy) as described herein.

Any appropriate cancer can be treated as described herein. For example, breast cancer, ovarian cancer, gastrointestinal cancer, stomach cancer, prostate cancer, lung cancer, bladder cancer, melanoma, or colorectal adenocarcinoma can be treated with (a) one or more inhibitors of UFM1 activity or expression and/or one or more inhibitors of UFL1 activity or expression together with and/or followed by (b) a DNA damaging therapy (e.g., radiation or chemotherapy) as described herein. In some cases, the (a) one or more inhibitors of UFM1 activity or expression and/or one or more inhibitors of UFL1 activity or expression and (b) a DNA damaging therapy (e.g., radiation or chemotherapy) can be administered sequentially, with the UFM1 and/or UFL1 inhibitors being administered first or with the DNA damaging therapy (e.g., radiation or chemotherapy) being administered first. In some cases, a cancer resistant to treatment with a DNA damaging therapy (e.g., radiation therapy or chemotherapy) such as irradiation (IR)-resistant prostate cancer can be treated using both (a) one or more inhibitors of UFM1 activity or expression and/or one or more inhibitors of UFL1 activity or expression and (b) a DNA damaging therapy (e.g., radiation or chemotherapy) either in combination or sequentially.

Any appropriate method can be used to identify a mammal having cancer. For example, imaging techniques and biopsy techniques can be used to identify mammals (e.g., humans) having cancer (e.g., breast cancer).

Once identified as having cancer (e.g., breast cancer, prostate cancer, or lung cancer), the mammal can be administered or instructed to self-administer (a) one or more inhibitors of UFM1 activity or expression and/or one or more inhibitors of UFL1 activity or expression to increase the sensitivity of cancer cells to treatment with a DNA damaging therapy (e.g., radiation or chemotherapy), (b) both (i) one or more inhibitors of UFM1 activity or expression and/or one or more inhibitors of UFL1 activity or expression and (ii) a DNA damaging therapy (e.g., radiation or chemotherapy) in combination, or (c) both (i) one or more inhibitors of UFM1 activity or expression and/or one or more inhibitors of UFL1 activity or expression and (ii) a DNA damaging therapy (e.g., radiation or chemotherapy) sequentially. When administered sequentially, UFM1 and/or UFL1 inhibitor(s) can be administered first. In some cases, when administered sequentially, the DNA damaging therapy (e.g., radiation or chemotherapy) can be administered first.

Examples of inhibitors of UFM1 activity or expression that can be used as described herein include, without limitation, peptidomimetic inhibitors, inhibitory anti-UFM1 antibodies, anti-sense molecules designed to inhibit UFM1 polypeptide expression, and nucleic acids designed to promote RNA interference of UFM1 polypeptide expression. In some cases, an inhibitor of UFM1 activity can be designed to disrupt UFM1 signaling. Examples of inhibitors of UFM1 activity designed to disrupt UFM1 signaling include, without limitation, molecules containing the peptide sequence WWSLGVIMY (SEQ ID NO:13). Examples of nucleic acids designed to promote RNA interference of UFM1 polypeptide expression include, without limitation, those nucleic acids (e.g., shRNA) that target CTGCGGATTATTCCTAGAGAT (SEQ ID NO:14), GCAGTCT- TAAAGTTTGCAGCA (SEQ ID NO:15), CCAATGATG-GAATAGGAATAA (SEQ ID NO:16), or GTGTTCCTGAAAGTACACCTT (SEQ ID NO:17) as well as siRNAs targeting UFM1 such as CGGAAGUGCUGAUGAGUUA (SEQ ID NO:18), GAGGAAAGCAACAGAGGAA (SEQ ID NO:19), CAAAUGAACAGCAGGAUUA (SEQ ID NO:20), or GGGAGAACUGAAAGGGAAA (SEQ ID NO:21).

Examples of inhibitors of UFL1 activity or expression that can be used as described herein include, without limitation, peptidomimetic inhibitors, inhibitory anti-UFL1 antibodies, anti-sense molecules designed to inhibit UFL1 polypeptide expression, and nucleic acids designed to promote RNA interference of UFL1 polypeptide expression. In some cases, an inhibitor of UFL1 activity can be designed to disrupt UFL1 signaling. Examples of inhibitors of UFL1 activity designed to disrupt UFL1 signaling include, without limitation, selumetinib (AZD6244). An exemplary structure for AZD6244 is as follows.

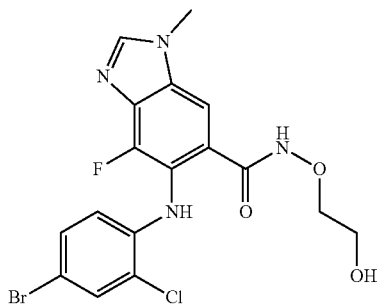 [SMILES: Cn1cnc2c(F)c(Nc3ccc(Br)cc3Cl)c(C(=O)NOCCO)cc21]

Examples of nucleic acids designed to promote RNA interference of UFL1 polypeptide expression include, without limitation, those nucleic acids (e.g., shRNA) that target GAAACACTTCTGTGTCAGAAA (SEQ ID NO:1), GCTCTGGAACATGGGTTGATA (SEQ ID NO:2), CCAGTAAGCATAAGTCATATT (SEQ ID NO:22), or GAGAGAGAACACATGCAATTT (SEQ ID NO:23) as well as siRNAs targeting UFL1 such as CAGAAGAGGUCAAUGAUAAUU (SEQ ID NO:24), UCAUAUGGGCAAAGGGAAAUU (SEQ ID NO:25), CAGAAGAGGUCAAUGAUAA (SEQ ID NO:26), and UCAUAUGGGCAAAGGGAAA (SEQ ID NO:27).

Examples of DNA damaging therapies that can be used as described herein include, without limitation, radiation, chemotherapeutic agents (e.g., cisplatin, carboplatin, 5-fluorouracil, and gemcitabine), alkylating agents, antimetabolites (e.g., methotrexate), intercalating agents (e.g., doxorubicin), anti-microtubule agents, topoisomerase inhibitors (e.g., etoposide), and PARP inhibitors (e.g., olaoarib).

In some cases, two or more inhibitors of UFM1 activity or expression (e.g., two, three, four, five, or more UFM1 inhibitors) can be administered to a mammal to increase the sensitivity of cancer cells to treatment with a DNA damaging therapy. In some cases, two or more inhibitors of UFL1 activity or expression (e.g., two, three, four, five, or more UFL1 inhibitors) can be administered to a mammal to increase the sensitivity of cancer cells to treatment with a DNA damaging therapy.

In some cases, one or more inhibitors of UFM1 activity or expression and/or one or more inhibitors of UFL1 activity or expression can be formulated into a pharmaceutically acceptable composition for administration to a mammal having cancer (e.g., breast cancer). For example, a therapeutically effective amount of an UFL1 polypeptide inhibitor (e.g., a peptidomimetic inhibitor) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

In some cases, (a) one or more inhibitors of UFM1 activity or expression and/or one or more inhibitors of UFL1 activity or expression and (b) a DNA damaging agent such as gemcitabine can be formulated together into a pharmaceutically acceptable composition for administration to a mammal having cancer (e.g., breast cancer, lung cancer, prostate cancer). For example, a therapeutically effective amount of a UFL1 polypeptide inhibitor (e.g., a peptidomimetic inhibitor) can be formulated together with one or more DNA damaging agents (e.g., doxorubicin). A pharmaceutical composition containing both (a) one or more inhibitors of UFM1 activity or expression and/or one or more inhibitors of UFL1 activity or expression and (b) a DNA damaging agent such as doxorubicin can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing (a) one or more inhibitors of UFM1 activity or expression and/or one or more inhibitors of UFL1 activity or expression with or without (b) a DNA damaging agent such as doxorubicin can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including (a) one or more inhibitors of UFM1 activity or expression and/or one or more inhibitors of UFL1 activity or expression with or without (b) a DNA damaging agent such as doxorubicin can be administered locally or systemically. For example, a composition provided herein can be administered locally by injection into tumors. In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments such as use of other agents, and the judgment of the treating physician.

An effective amount of a composition containing one or more inhibitors of UFM1 activity or expression and/or one or more inhibitors of UFL1 activity or expression can be any amount that increases the sensitivity of cancer cells to treatment with a DNA damaging therapy without producing significant toxicity to the mammal. For example, an effective amount of an UFM1 or UFL1 polypeptide inhibitor can be from about 10 mg/kg to about 100 mg/kg (e.g., about 10 mg/kg to about 75 mg/kg, about 10 mg/kg to about 50 mg/kg, about 10 mg/kg to about 25 mg/kg, about 25 mg/kg to about 100 mg/kg, about 50 mg/kg to about 75 mg/kg, about 25 mg/kg to about 75 mg/kg, about 35 mg/kg to about 65 mg/kg, or about 45 mg/kg to about 55 mg/kg). In some cases, from about 0.75 g to about 7.5 g (e.g., about 0.75 g to about 6 g, about 0.75 g to about 5 g, about 0.75 g to about 2.5 g, about 1 g to about 7.5 g, about 2.5 g to about 7.5 g, about 3.5 g to about 7.5 g, about 5 g to about 7.5 g, about 1.5 g to about 6.5 g, or about 2.5 g to about 5.5 g) of an UFM1 or UFL1 polypeptide inhibitor can be administered to an average sized human (e.g., about 75-85 kg human) within a 24-hour period of time.

An effective amount of a composition containing one or more DNA damaging agents can be any amount that reduces the number of cancer cells present within the mammal without producing significant toxicity to the mammal. In some cases, an effective amount of a composition containing one or more DNA damaging agents can be an amount that, when used in connection with an inhibitor of UFM1 activity or expression and/or an inhibitor of UFL1 activity or expression, reduces the number of cancer cells present within the mammal to a level greater than that observed when that amount is used in the absence of the UFM1 and/or UFL1 inhibitors.

In some cases, an effective amount of a DNA damaging agent such as olaoarib when used with UFM1 and/or UFL1 inhibitors (either in combination or sequentially) can be from about 10 mg/kg to about 50 mg/kg. In some cases, from about 0.75 g to about 3.75 g of a DNA damaging agent can be administered to an average sized human (e.g., about 75-85 kg human) within a 24-hour period of time.

If a particular mammal fails to respond to a particular amount, then the amount of the UFM1 and/or UFL1 inhibitors and/or DNA damaging agent can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of one or more inhibitors of UFM1 activity or expression and/or one or more inhibitors of UFL1 activity or expression and/or a DNA damaging therapy can be any amount that reduces the number of cancer cells present within the mammal without producing significant toxicity to the mammal. For example, the frequency of administration of a combination containing both (a) one or more inhibitors of UFM1 activity or expression and/or one or more inhibitors of UFL1 activity or expression and (b) a DNA damaging therapy can be from about daily to about four times a month.

The frequency of administration of one or more inhibitors of UFM1 activity or expression and/or one or more inhibitors of UFL1 activity or expression and/or a DNA damaging therapy can remain constant or can be variable during the duration of treatment. A course of treatment with a composition containing an UFM1 and/or UFL1 polypeptide inhibitor(s) and/or a DNA damaging agent can include rest periods. For example, a composition containing one or more UFL1 polypeptide inhibitors can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more inhibitors of UFM1 activity or expression and/or one or more inhibitors of UFL1 activity or expression can be any duration that increases the sensitivity of cancer cells to treatment with a DNA damaging therapy without producing significant toxicity to the mammal. In some cases, the effective duration can vary from several days to several weeks. In general, the effective duration for increasing the sensitivity of cancer cells to treatment with a DNA damaging therapy can range in duration from about one week to about six weeks.

In some cases, an effective duration for administering a composition containing one or more inhibitors of UFM1 activity or expression and/or one or more inhibitors of UFL1 activity or expression with a DNA damaging therapy can be any duration that reduces the number of cancer cells present within the mammal without producing significant toxicity to the mammal. In some cases, the effective duration can vary from several days to several weeks. In general, the effective duration for reducing the number of cancer cells present within the mammal can range in duration from about three weeks to about six weeks.

Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment, the number of cancer cells present within a mammal, and/or the severity of one or more symptoms related to the condition being treated (e.g., cancer) can be monitored. Any appropriate method can be used to determine whether or not the number of cancer cells present within a mammal is reduced. For example, imaging techniques can be used to assess the number of cancer cells present within a mammal.

This document also provides methods and materials for identifying mammals (e.g., humans) having cancer (e.g., prostate cancer) that is susceptible to treatment with a DNA damaging therapy (e.g., radiation or chemotherapy). For example, cancer cells obtained from a mammal can be assessed for the presence of a reduced level of UFM1 and/or UFL1 polypeptide expression. Any appropriate method can be used to determine if cancer cells express a reduced level of UFM1 and/or UFL1 polypeptides. For example, nucleic acid-based assays such as RT-PCR can be used to measure reduced mRNA levels within cancer cells. In some cases, immunoassays such as ELISAs, FACS, or cell staining using antibodies (e.g., anti-UFM1 antibodies and/or anti-UFL1 antibodies) can be used to detect the presence of a reduced level of UFM1 and/or UFL1 polypeptides within cancer cells. The term "reduced" as used herein with respect to UFM1 and/or UFL1 expression levels can be any level less than (e.g., at least 5, 10, 20, 30, 40, 50, 75, 85, 95, or more percent less than) the median level observed in cancer cells having fully functional DDR obtained from a random sampling of mammals having cancer. In some cases, the term "reduced" as used herein with respect to UFM1 and/or UFL1 expression levels can be any level less than (e.g., at least 5, 10, 20, 30, 40, 50, 75, 85, 95, or more percent less than) the median level observed in U2OS cancer cell line (ATCC Deposit No. HTB-96.

Those mammals with cancer cells having a reduced level of UFM1 and/or UFL1 polypeptide expression can be classified as being susceptible to treatment with a DNA damaging therapy (e.g., radiation or chemotherapy). In some cases, a mammal (e.g., a human) having cancer can be treated by (a) detecting the presence of a reduced level of UFM1 and/or UFL1 polypeptide expression in the cancer cells, and (b) administering a DNA damaging therapy (e.g., radiation or chemotherapy) to the mammal.

The invention will be further described in the following examples, which do not limit the scope of the invention described in the claims.

EXAMPLES

Example 1—Increasing the Sensitivity of Cancer Cells to Treatment with Ionizing Radiation Cell Culture, Plasmids, Antibodies and Transfection Reagents U2OS, HeLa-DR-GFP, U2OS (TA-induced system), and 293T cells were cultured in DMEM supplemented with 10% FBS. NBST cells were cultured in DMEM supplemented with 15% FBS. MDA-MB-231 ROS8 cells were cultured in DMEM supplemented with 10% FBS and Zeocin and Blasticidin treatment. All cell lines were kept in a humidified 37° C. (5% $CO_2$ 5% $O_2$) incubator.

Ufm1ΔC2-Flag-His, UBA5-GST, UFBP-GST, UFC-GST, and UFL1-MBP plasmids are described elsewhere (Komatsu et al., *Embo J*, 23:1977-1986 (2004)). UFL1-myc (Yoo et al., *Mol. Cell*, 56:261-274 (2014)) was used as template and UFL1 PCR product were inserted into pIRES vector with Flag-S-SBP Tag. UFL1S462A mutant was generated by site-mutagenesis kit.

Anti-UFL1 antibody for western blot, anti-Nbs1 antibody, and anti-RIF1 antibody were obtained from Bethyl. Anti-actin, anti-UFL1 for detecting foci, and anti-STK38 antibodies for detecting foci were obtained from Sigma. Anti-ATM, anti-pSer1981 ATM, anti-Mre11, anti-Rad50, anti-Suv39h1, anti-Cul4A, anti-SQ/TQ motif, anti-Chk2, and anti-phosphoChk2 antibodies were obtained from Cell Signaling. Anti-Tip60, anti-53BP1, anti-MDC1, anti-Suv39h1, and anti-γH2AX antibodies were obtained from Millipore. Anti-H2A, anti-H2B, anti-H3, anti-H4, and anti-H3K9Me3 were obtained from Abcam. Anti-UFM1 and anti-BRCA1 antibodies were obtained from Santa Cruz.

Lipofectamine 2000 Transfection Reagent (Invitrogen) and Minis TransIT Transfection Reagent (Mirus Bio LLC) were used for carrying out transfections following the manufacturer's protocols.

RNA Interference

UFL1 shRNA sh1 (oligo1: GAAACACTT-CTGTGTCAGAAA; SEQ ID NO:1, targeting 3'UTR), (oligo2: GCTCTGGAACATGGGTTGATA; SEQ ID NO:2, targeting CDS) were inserted into Tet-on PLKO.1 vector. Cul4A shRNA sh1 (target sequence: GCAGAACT-GATCGCAAAGCAT; SEQ ID NO:3) and sh2 (target sequence: GGACAAGAAGATGTTACTAAA; SEQ ID NO:4) were obtained from Sigma. DDB1 shRNA1 (target sequence: CGACCGTAAGAAGGTGACTTT; SEQ ID NO:5) and sh2 (target sequence: CCTTGATTGGTGTT-GCCAGTT; SEQ ID NO:6) were obtained from Sigma. Lentiviruses were made according to manufacturer's protocol. Tip60 siRNA was obtained from Santa Cruz. STK38 siRNA1 (5'-CGUCGGCCAUAAACAGCUdTT-3'; SEQ ID NO:7, targeting 3'-UTR) and STK38 siRNA2 (5'-GC-CUGCAACUUAGGCGGAUUGdTT-3'; SEQ ID NO:8, targeting CDS) were obtained from Qiagen.

Western Blot and Immunoprecipitation

Cells were lysed with NETN buffer (20 mM Tris-HCl, pH 8.0, 100 mM NaCl, 1 mM EDTA, 0.5% Nonidet P-40 with 50 mM b-glycerophosphate, 10 mM NaF, and 1 mg/mL each of pepstatin A and aprotinin). After centrifugation, the supernatant was removed and incubated with antibody and protein A or protein G Sepharose beads (Amersham Biosciences) for 2 hours or overnight at 4° C. The samples were separated by SDS-PAGE following three washes with NETN buffer. Western blots were carried out following standard procedures.

Chromatin Fraction

Chromatin fraction assays were performed as described elsewhere (Liu et al., Mol. Cell, 56:681-695 (2014)). Briefly, cells were harvested and lysed with NETN buffer with low salt (20 mM Tris-HCl, pH 8.0, 10 mM NaCl, 1.5 mM $MgCl_2$, 1 mM EDTA, 0.5% Nonidet P-40, 20 mM NaF, 1 mM $Na_3VO_4$, 1 μg/mL aprotinin, and 1 μg/mL pepstatin). The chromatin pellet was washed with PBS three times and later resuspended in 0.2 M HCl for 30 minutes on ice. The soluble extraction was neutralized with 1 M NaOH for western blot.

His-UFM1 Purification

Cells stably expressing Ufm1ΔC2-Flag-His were irradiated with IR and then lysed with denaturing buffer with 8 M urea 50 mM $Na_2HPO_4$ pH 8.0, 0.3 M NaCl and 1 mM PMSF. After sonication, the supernatant was incubated with nickel bead for 2 hours. Following three washes with buffer containing 8 M Urea, 50 mM $Na_2HPO_4$ pH 8.0, 0.5 M NaCl and 10 mM imidazole, the beads was boiled with SDS sample buffer. The samples were separated by SDS-PAGE and stained with Coomassie blue. The gel was cut, and proteins were detected by mass spectrometry was performed.

In Vitro Ufmylation Assay

In vitro ufmylation assays were performed as described elsewhere (Tatsumi et al., *J. Biol. Chem.*, 285:5417-5427 (2010)). Briefly, UBA5, UFC1, UFM1, UFBP1, and UFL1 polypeptides were produced and purified from *E. coli*. Purified recombinant polypeptides were dialyzed with buffer containing 50 mM Tris (pH 8.5), 150 mM NaCl, and 1 mM dithiothreitol. The purified polypeptides Ufm1ΔC2, Uba5, Ufc1, UFBP1, MBP-Ufl1, and Histone H4, H3, H2A or H2B (NEB) were added into the reaction buffer containing 5 mM ATP and 10 mM $MgCl_2$ and then incubated at 30° C. for 90 minutes. SDS sample buffer containing 5% β-mercaptoethanol was added into the mixture to stop the reaction.

Homologous Recombination Assay

HeLa DR-GFP cells are described elsewhere (Moynahan et al., *Mol. Cell*, 7:263-272 (2001)). Cells infected with UFL1 Tet-on shRNA viruses or control viruses were treated with doxycyclin for 5 days, and then were transfected with pCBA-I-SceI and pCherry. Two days later, cells were harvested and analyzed by fluorescence-activated flow cytometry (FACS) to examine GFP positive cells. Results were normalized to control group.

NHEJ Assay

The in vivo end-joining reporter plasmid pEGFP-Pem1-Ad2 was described elsewhere (Seluanov et al., *Proc. Natl. Acad. Sci. USA*, 101:7624-7629 (2004)). Briefly, linearized pEGFP-Pem1-Ad2 and pCherry were co-transfected into UFL1 depleted or control cells. 48 hours later, cells were harvested and fixed with 2% paraformaldehyde, and then analyzed by FACS (Calibur instrument, BD Biosciences).

Immunofluorescence Staining

Cells were seeded on coverslips and then fixed with 3% paraformaldehyde on ice at indicated timepoints after IR treatment, washed with PBS, and permeabilized for 10 min with 0.5% Triton X-100. Cells were blocked with 5% goat serum and then incubated with primary antibody for 1 hour at room temperature. After washing with PBS, FITC or Rhodamine conjugated secondary antibody (Jackson ImmunoResearch) was added and incubated for 30 minutes at room temperature. After two PBS washes, cells were counterstained with 4'6-diamidino-2-phenylindole (DAPI). Finally, the coverslips were mounted with glycerin containing paraphenylenediamine.

Inducible Single DSB System

U2OS cells stably expressing RFP-I-SceI-GR were described elsewhere (Zeitlin et al., *Proc. Natl. Acad. Sci. USA*, 106:15762-15767 (2009)). The synthetic glucocorticoid (GR) ligand triamcinolone acetonide (TA obtained from Sigma) was added (0.1 μM) into medium and induce the translocation of RFP-I-SceI-GR from cytoplasm into nucleus. Photos were taken using a Nikon eclipse 80i fluorescence microscope.

Chromatin Immunoprecipitation Assay

MDA-MB-231ROS8 cells were used for ChIP assay. One day after transfection of I-SceI, about $5 \times 10^7$ cells were treated with 1% formaldehyde for 10 minutes at room temperature to crosslink proteins to DNA. Glycine was added and incubated at room temperature for 5 minutes to stop the cross-linking. Cells were harvested, and the pellets were resuspended in cell lysis buffer (5 mM Pipes (KOH), pH 8.0, 85 mM KCl, 0.5% NP-40) containing the following protease inhibitors 1 μg/mL leupeptin, 1 μg/mL aprotinin, and 1 mM PMSF, and incubated for 10 minutes on ice. Nuclei were pelleted by centrifugation (5000 rpm for 5 minutes). Nuclei were then resuspended in nuclear lysis buffer (50 mM Tris, pH 8.1, 10 mM EDTA, 1% SDS containing the same protease inhibitors as in cell lysis buffer) and sonicated to shear chromatin to an average size of 0.6 kb. Once centrifuged until clear, the lysates were precleared overnight with salmon sperm DNA/protein-A agarose slurry. 20% of each supernatant was used as input control and processed with the cross-linking reversal step. The rest of the supernatant (about 80% of the total) was incubated with 5 μg of the indicated antibody overnight at 4° C. with rotation. Complexes were washed four times, once in high salt buffer (50 mM Tris-Cl, pH 8.0, 500 mM NaCl, 0.1% SDS, 0.5% deoxycholate, 1% NP-40, 1 mM EDTA), once in LiCl buffer (50 mM Tris-Cl, pH 8.0, 250 mM LiCl, 1% NP-40, 0.5% deoxycholate, 1 mM EDTA) and twice in TE buffer (10 mM Tris-Cl, pH 8.0, 1 mM EDTA, pH 8.0). Beads were resuspended in TE containing 50 mg/mL of RNase and incubated for 30 minutes. Beads were washed with water, and elution buffer (1% SDS, 0.1 M NaHCO$_3$) was added for 15 minutes. Crosslinks were reversed by adding 10 μg/mL RNAse and 5M NaCl to a final concentration of 0.3 M to the eluents and incubate in a 65° C. water bath for 4-5 hours. Two volumes of 100% ethanol were added to precipitate overnight at −20° C. DNA was pelleted and resuspended in 100 μL of water, 2 μL of 0.5 M EDTA, 4 μL 1 M Tris, pH 6.5, and 1 μL of 20 mg/mL Proteinase K and incubated for 1-2 hours at 45° C. DNA was then purified and used in PCR reactions.

The PCR primers for ChIP, about 220 bp away from the I-SceI cut site, were as follows: Forward: 5'-TACAGCTCCTGGGCAACGTG-3' (SEQ ID NO:9); Reverse: 5'-TCCTGCTCCTGGGCTTCTCG-3' (SEQ ID NO:10). Amplification was performed using the following program: 95° C./5 minutes, 1 cycle; 95° C./45 seconds, 56° C./30 seconds, and 72° C./30 seconds, 30 cycles; 72° C./10 minutes, 1 cycle. As an internal control for the normalization of the specific fragments amplified, a locus outside the region of the DSB was amplified, in this case FKBP5, using the input control sample as template. The internal control (FKBP5) primers were as follows: Forward: 5'-CAGTCAAGCAATGGAAGAAG-3' (SEQ ID NO:11); Reverse: 5'-CCCGTGCCACCCCTCAGTGA-3' (SEQ ID NO:12). After Q-PCR amplification, the FKBP5 input controls for untransfected (no DSB) and I-SceI transfected (DSB) cells were used to normalize the untransfected and transfected samples respectively. After normalization, the relative levels of the indicated proteins on a DSB were calculated using the formula: (IP I Sce-1/Input ISce-1)/(IP untransfected/Input untransfected). All Q-PCR reactions were performed in triplicate, with the SEM values calculated from three independent experiments.

Statistical Analysis

Comparisons were carried out with a two-tailed unpaired Student's t test (* indicates $p<0.05$, ** indicates $p<0.01$). Results were presented as mean±standard error of mean (SEM).

Results

Figure 1B:
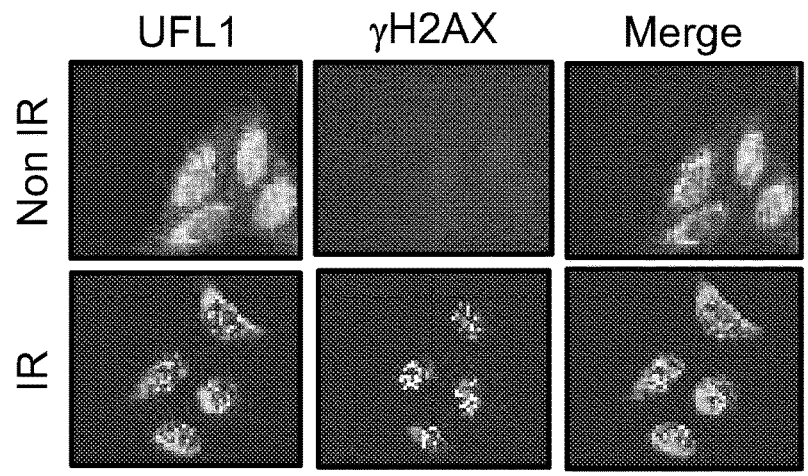
Figure 1C:
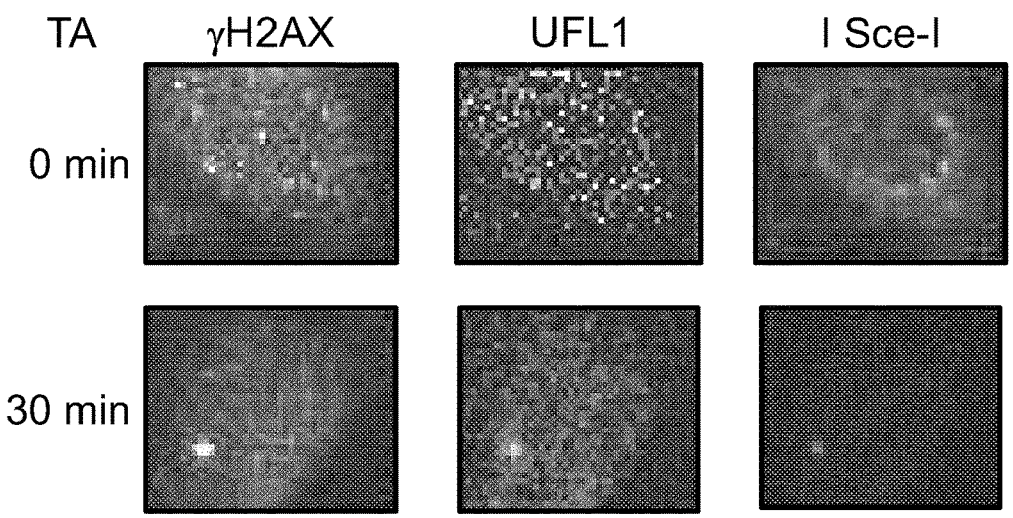

UFL1 was found to interact with the MRN complex in a DNA damage-inducible manner (FIG. 1a). It was hypothesized that UFL1 might be involved in the DDR. Following DNA damage, various polypeptides involved in DDR pathways, such as MDC1, BRCA1 and 53BP1, aggregate at DNA lesions and help DDR signaling and DNA repair. The following was performed to test whether UFL1 localized to the sites of DNA damage. Under unstressed condition, UFL1 mainly localized in the cytoplasm and nucleus in a diffused pattern. However, following ionizing irradiation (IR), nuclear UFL1 protein formed discrete nuclear foci and colocalized with γH2AX (FIG. 1b), indicating that UFL1 relocalized to DNA lesions. To further confirm this finding, an inducible double strand break (DSB) system, in which addition of triamcinolone acetonide (TA) induced expression of I-SceI and created a single DSB in the genomic DNA, was utilized. UFL1 was found to accumulate at DSB site after TA treatment for 30 minutes (FIG. 1c). These results suggested that UFL1 might play a role in the DDR.

Figure 1D:
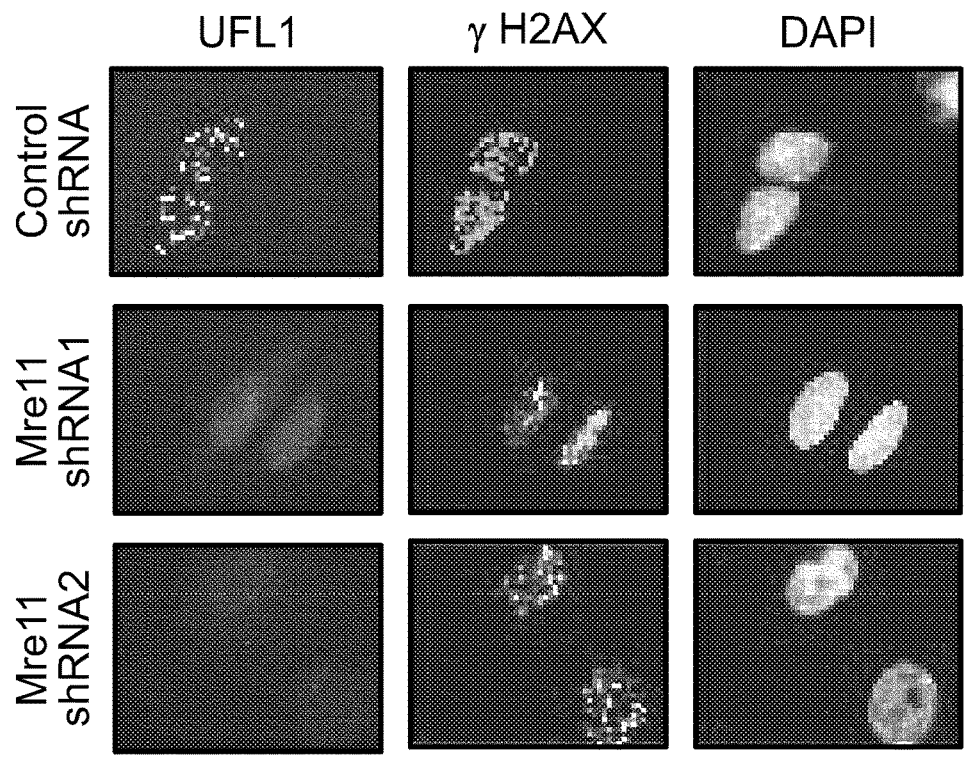
Figure 1E:
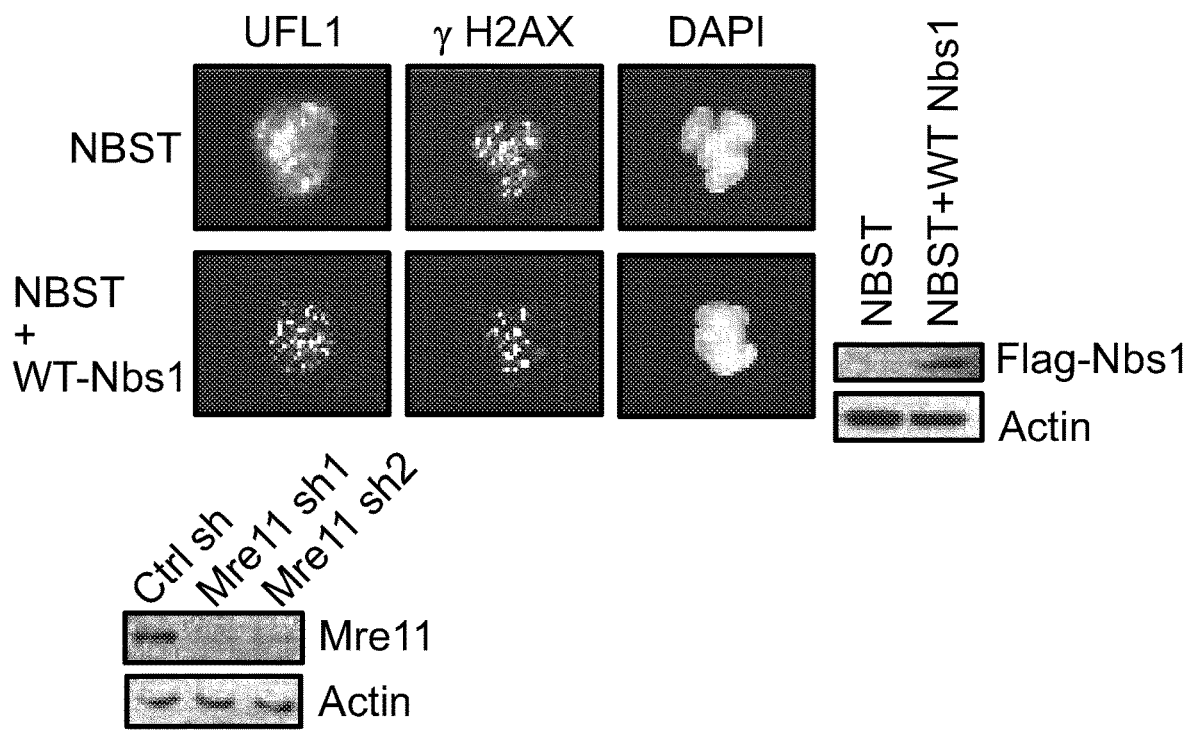
Figure 1F:
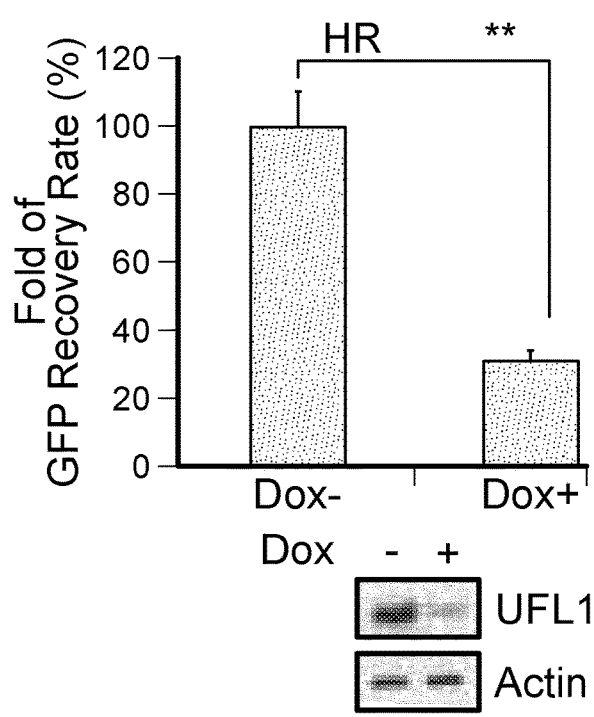
Figure 1G:
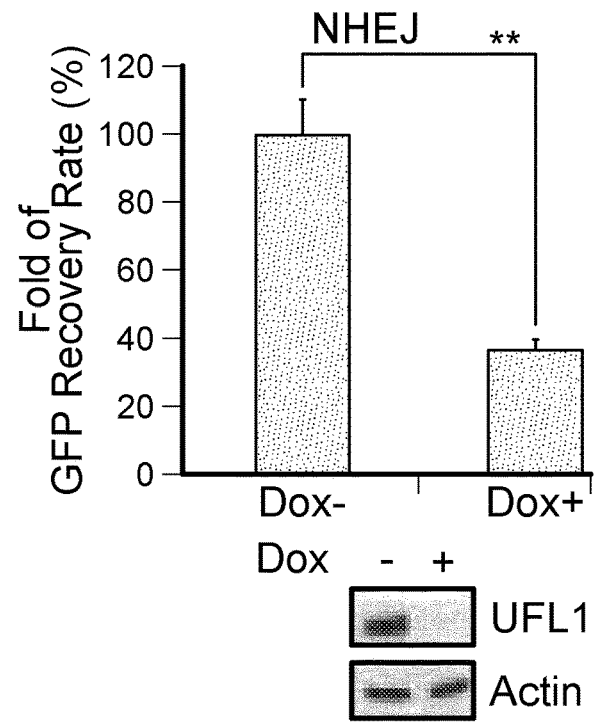
Figure 2A:
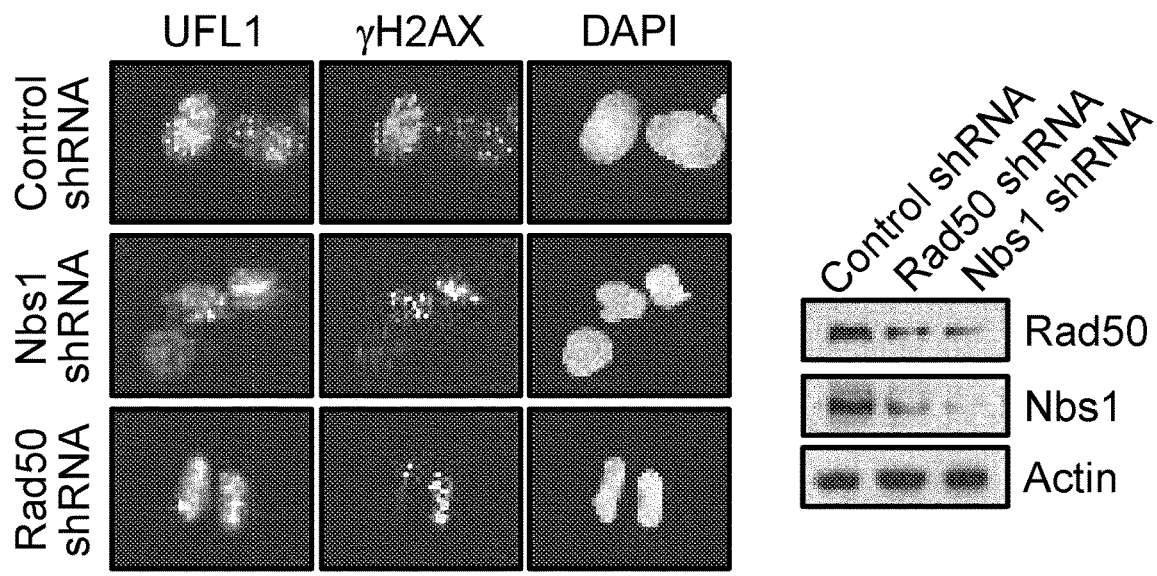
FIG. 2. UFL1 is recruited to DSBs by the MRN complex and regulates ATM signaling. a, Immunofluorescence of UFL1 and γH2AX in Nbs1 or Rad50 depleted U2OS cells after IR (2 Gy for all immunofluorescence experiments). b, U2OS cells were infected with viruses encoding UFL1 Tet-on shRNAs and then incubated with doxycycline (Dox) for 5 days. The lysates were blotted with the indicated antibodies. c-d, HeLa cells integrated with HR reporter or transfected with NHEJ reporter were depleted of UFL1 and subjected to the (c) HR assay or (d) NHEJ assay as described in the method. Percentage of positive cell was compared to the control group. Data presented as mean±SEM. of three biological triplicates. P<0.01. e-h, Time course of 53BP1, BRCA1, RIF1, and MDC1 foci formation in control or UFL1 knockdown cells. The data presented are mean±SEM for three independent experiments. p<0.01. i, ATM signaling in cells expressing inducible UFL1 shRNA2 1 h after 10 Gy IR.

The following was performed to test how UFL1 was recruited to DNA lesions. Because of its interaction with the MRN complex, the MRN complex was tested for involvement in UFL1 recruitment. Depletion of Mre11 was found to attenuate UFL1 and γH2AX foci formation (FIG. 1d). Furthermore, knockdown of Nbs1 or Rad50 also suppressed UFL1 and γH2AX foci formation (FIG. 2a). To further confirm this, the Nbs1 deficient cell line NBST (Wu et al., *Proc. Natl. Acad. Sci. USA,* 105:11200-11205 (2008)) was utilized. In NBST cells, UFL1 failed to form nuclear foci following DNA damage, while reconstitution of WT Nbs1 resulted in the accumulation of UFL1 to DSBs (FIG. 1e). These results suggest that the MRN complex is involved in UFL1 recruitment to DSBs.

Figure 1H:
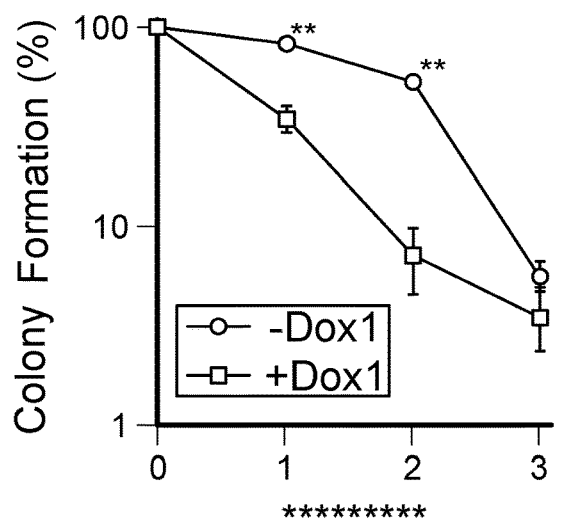
Figure 2B:
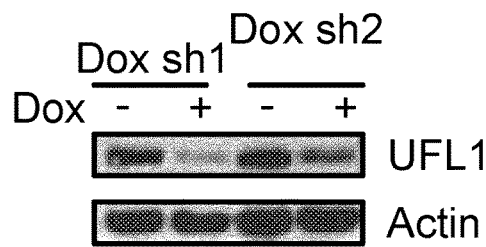
Figure 2C:
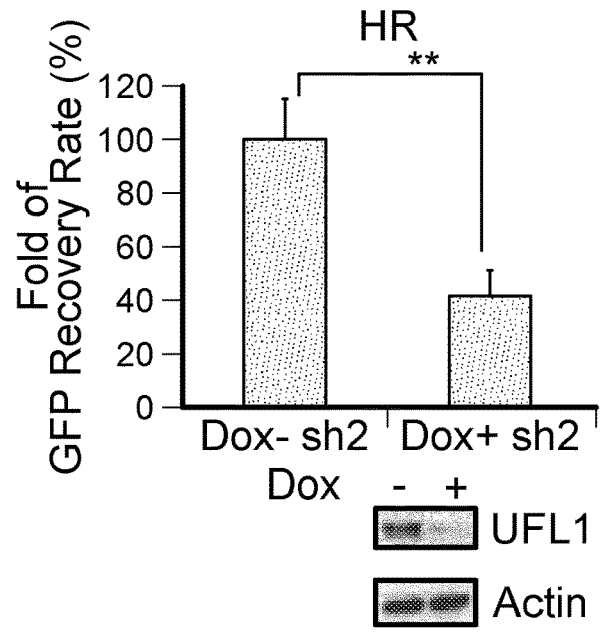
Figure 2D:
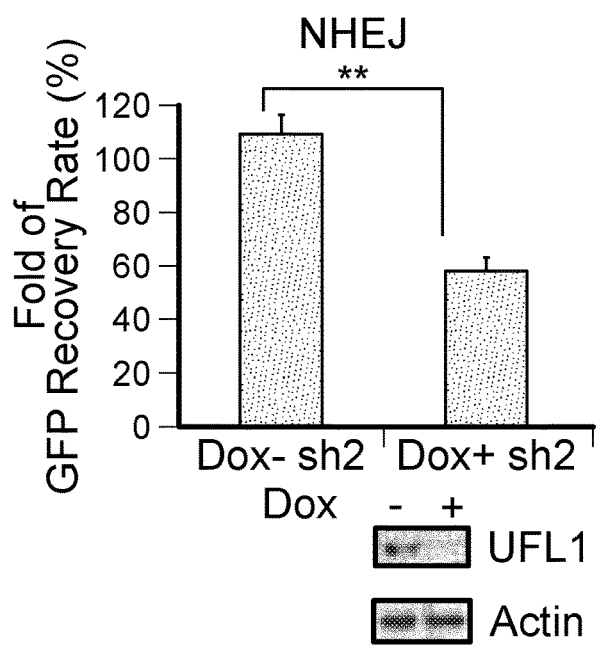
Figure 2E:
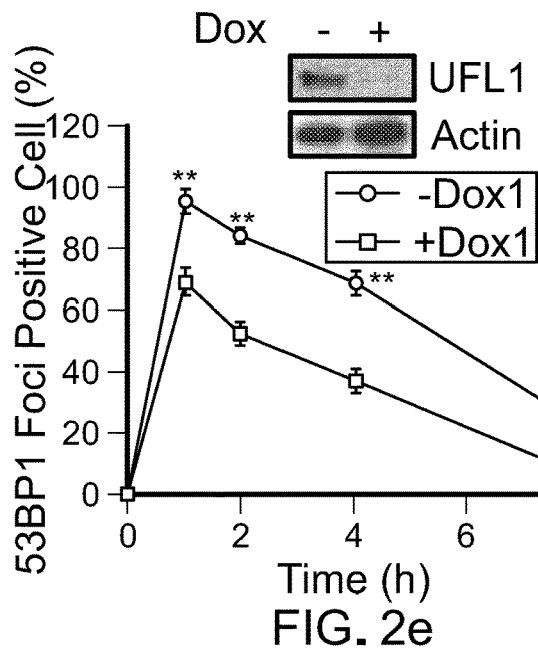
Figure 2F:
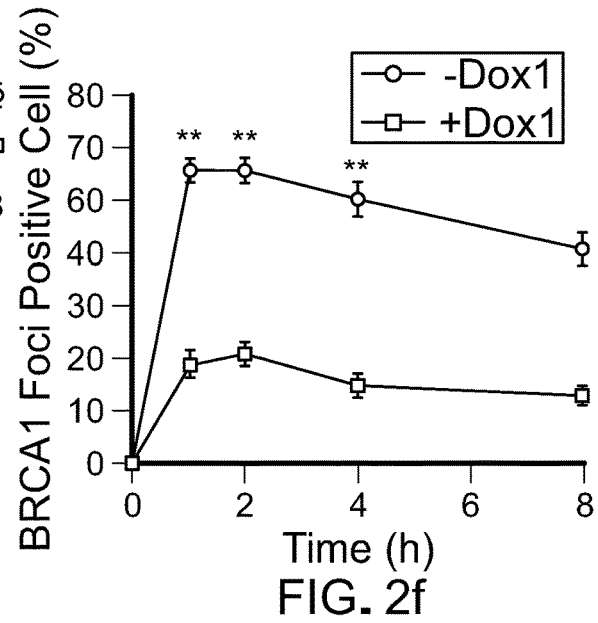
Figure 2G:
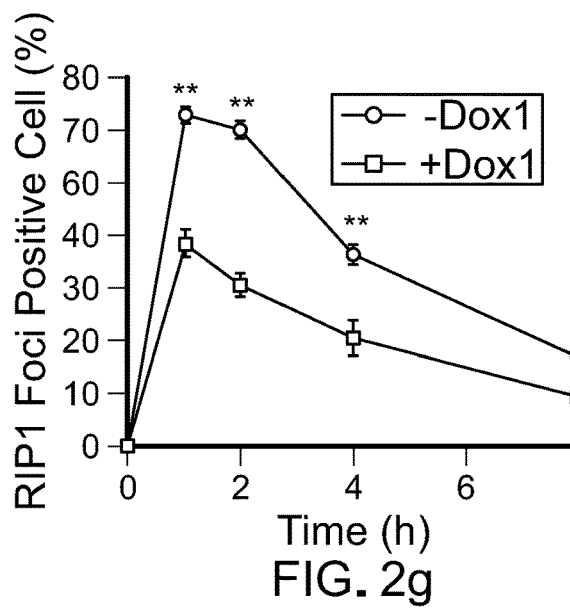

How UFL1 affected DNA repair and DDR signaling was examined. To analyze the effect of UFL1 on the two major DNA DSB repair pathways, homologous recombination (HR) and non-homologous-mediated end joining (NHEJ), HR and NHEJ reporter systems were utilized. A doxycycline (Dox) inducible system was used to express UFL1 shRNAs. After Dox treatment, UFL1 expression was significantly suppressed for two independent shRNAs (FIG. 2b). Both HR and NHEJ were compromised in UFL1 depleted cells (FIG. 1f-1g and FIG. 2c-2d). Consistently, cells depleted of UFL1 were more sensitive to IR treatment in clonogenic survival assays (FIG. 1h). Because BRCA1 and 53BP1 regulates HR and NHEJ pathways, respectively (Chen et al., *Cancer Res.,* 59:1752s-1756s (1999); and Bunting et al., *Cell,* 141:243-254 (2010)), 53BP1 and BRCA1 foci formation in UFL1 depleted cells was examined. Impaired 53BP1 and BRCA1 foci formation was found in UFL1-depleted cells (FIG. 2e-f). In addition, foci formation of RIF1, which is one of 53BP1 binding proteins and participates in NHEJ repair, was also compromised (FIG. 2g). These results suggest that UFL1 regulates both HR and NHEJ pathways.

Figure 1I:
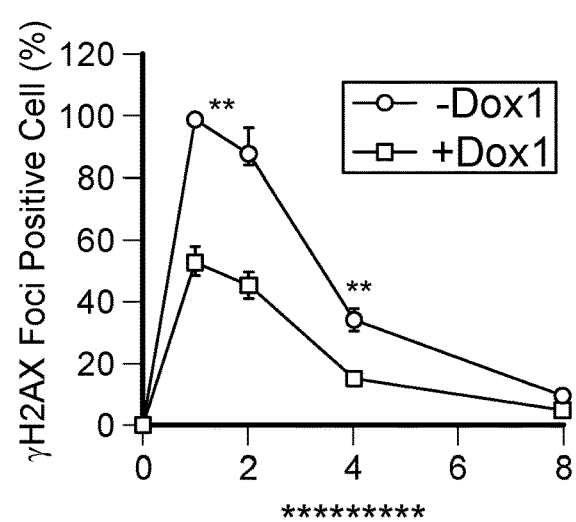
Figure 2H:
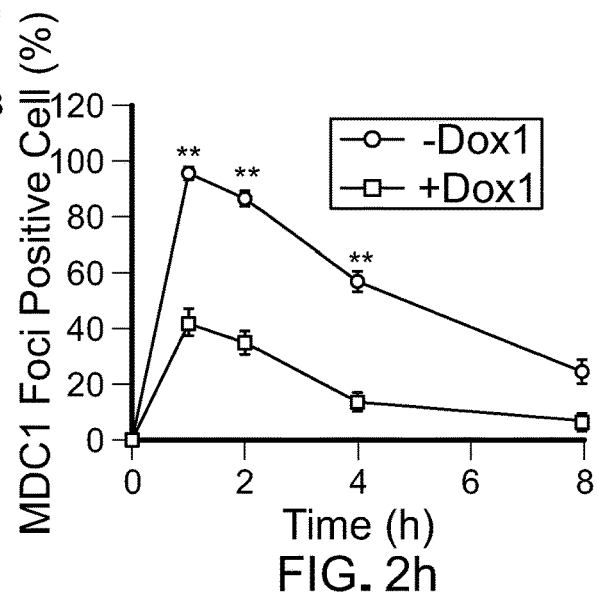

How UFL1 regulates BRCA1 and 53BP1 foci formation was examined. Interestingly, the foci formation of MDC1 and γH2AX also decreased in cells with knockdown of UFL1 (FIG. 2h and FIG. 1i). These results suggest that UFL1 functions at the earliest stage of DDR signaling. ATM is the primary transducers of DSB response that is activated in a MRN complex and Tip60 dependent manner (Shiloh and Ziv, *Nat. Rev. Mol. Cell Biol.,* 14:197-210 (2013)). Once ATM is activated, it phosphorylates downstream DDR factors, such as H2AX, MDC1, and Chk2 to initiate DDR signaling (Burma et al., *J. Biol. Chem.,* 276:42462-42467 (2001); and Rogakou et al., *J. Biol. Chem.,* 273:5858-5868 (1998)). Because UFL1 interacts with the MRN complex and regulate γH2AX foci formation, whether UFL1 regulates ATM activation was evaluated. By using phosphorylation of ATM at serine 1981 as a functional readout, loss of UFL1 significantly reduced ATM phosphorylation, but not ATM protein levels. Loss of UFL1 also reduced IR induced Chk2 phosphorylation (FIG. 1j and FIG. 2i). The protein level of other factors involved in ATM activation such as the MRN complex, Tip60, c-Abl, and Suv39h1 also were not altered. In addition, DNA-PK phosphorylation in response to IR was not affected (FIG. 1j). Reconstitution of wild-type UFL1 in UFL1-depleted cells restored ATM and Chk2 phosphorylation (FIG. 1k). In another experiment, UFSP2, which functions as a deufmylases to cleave UFM1 chain from its substrates (Kang et al., *J. Biol. Chem.,* 282:5256-5262 (2007)), was overexpressed. Overexpression of UFSP2 also suppressed ATM activation (FIG. 1l). Collectively, these results suggest that UFL1-mediated Ufm1 signaling regulates ATM activation.

Figure 4C:
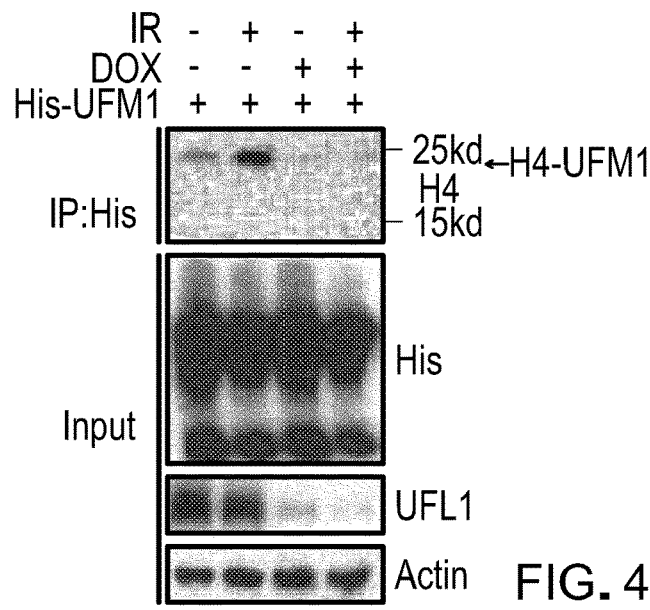
FIG. 4. UFL1 monoufmylates Histone H4 and promotes ATM activation. a, List of ufmylated proteins identified by mass spectrometric analysis from non-irradiated His-UFM1 expressing 293T cell. b, His-ufmylated proteins were purified from 293T cells before and after IR and detected with the indicated antibodies. c, His-ufmylated H4 was purified from control and UFL1 knockdown cells. d, In vitro ufmylation assay. Purified UBA5, UFC1, UFL1, UFM1, UFBP1 and H4 proteins were mixed together in the presence of ATP and $MgCl_2$ at 30° C. for 90 min. e, Ufmylation of 11 different histone H4 lysine mutants. f, ATM signaling in U2OS cells expressing WT histone H4 or H4K31R after IR. g, Colony formation of U2OS cells expressing WT histone H4 or H4K31R. The data presented are mean±SEM for three independent experiments. **p<0.01. h, Tip60 was detected in chromatin fractionation of irradiated U2OS cells. i-j, Analysis of H3K9 trimethylation and Suv39h1 recruitment by Chromatin IP (ChIP) at DSB sites from MDA-MB-231 ROS8 cells with indicated treatment. The data presented are mean±SEM for three independent experiments. *p<0.05, **p<0.01.
Figure 4D:
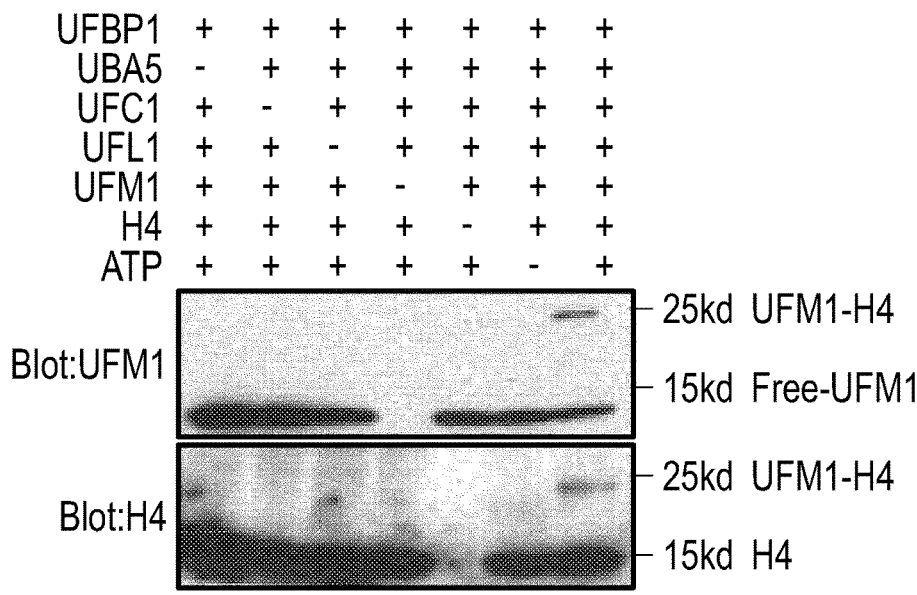
Figure 4E:
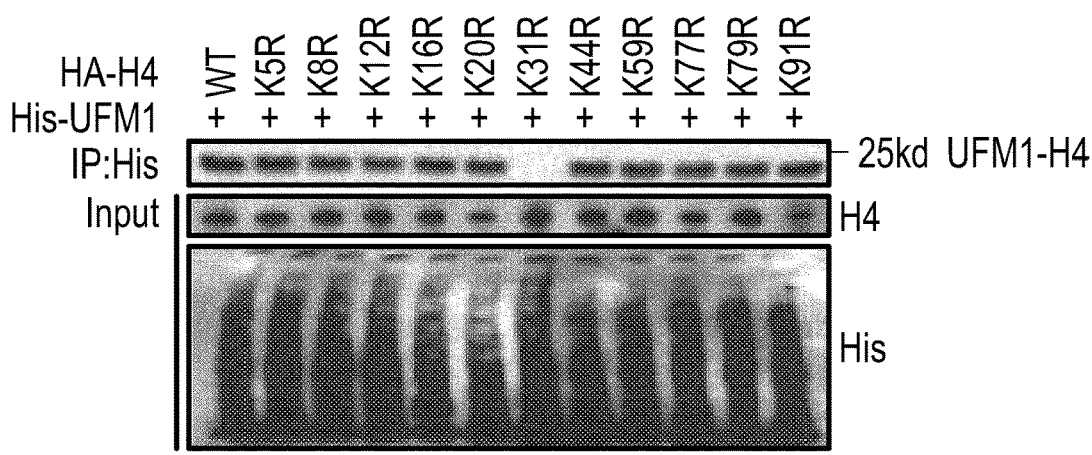
Figure 4F:
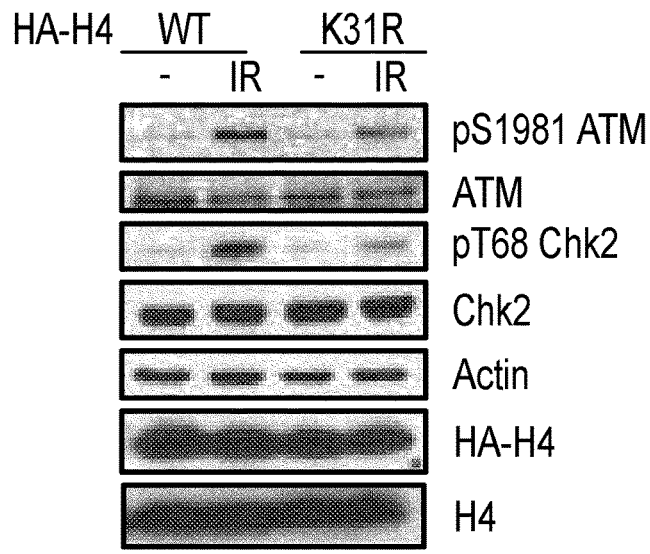
Figure 4G:
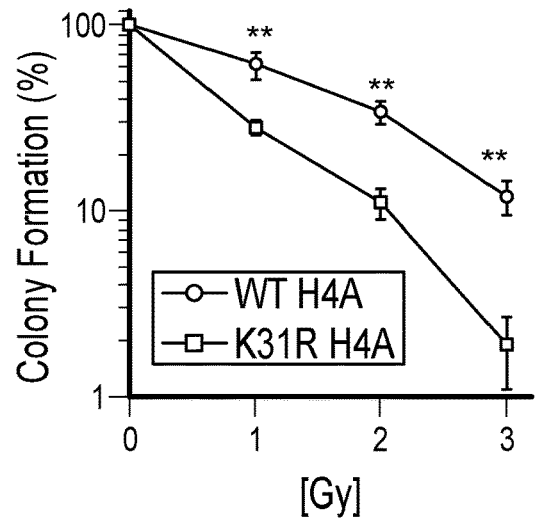

The MRN complex could be ufmylated following DNA damage. However, significant ufmylation of the MRN complex was not detected (FIG. 3a). ATM or Tip60 ufmylation was not detected either (FIG. 3a). To identify the substrates of UFL1 involved in ATM activation, His-Ufm1 modified proteins were purified under denaturing conditions. Mass spectrometry data suggested histone H4 might be one of the major Ufm1 modified substrates (FIG. 4a). To verify the mass spectrometry results, nickel affinity beads were used to pull down His tagged Ufm1. Histone H4, but not other histones, was found to be modified by Ufm1, and this modification was inducible by DNA damage (FIG. 4b). Furthermore, depletion of UFL1 alleviated H4 ufmylation (FIG. 4c). UFM1 is an ubiquitin like protein, and its mature protein molecular weight is about 9 kDa. Judged from the molecular weight of modified histone H4, it is likely to be mono-ufmylated. To determine whether H4 is a genuine substrate of UFL1, purified ufmylation factors were used, and an in vitro ufmylation assay was performed. Histone H4 was mono-ufmylated by UFL1 in vitro (FIGS. 4d and 3b). However, histone H3, H2A or H2B could not be modified by UFL1 (FIG. 3b). Histone H4 contains 11 lysines. To pin down the histone H4 ufmylation site, each lysine was individually mutated to arginine. Mutation of K31 totally abolished Ufm1 signal, suggesting that K31 was the only ufmylation site (FIG. 4e). To further confirm if K31 is important for ATM activation, wildtype (WT) histone H4 and the K31R mutant constructs were transfected into cells. Notably, histone H4 K31R expression inhibited ATM signaling (FIG. 4f). Furthermore, cells expressing H4K31R exhibited increased sensitivity to IR (FIG. 4g). Collectively, these findings suggest that UFL1 preferentially ufmylates histone H4 at K31, which is important for ATM activation and proper DDR. Histone H4 lysine 31 is also reported to be monoubiquitinated by Cul4A E3 complex, which then potentiates gene transcription (Kim et al., *Cell Reports,* 5:1690-1703 (2013)). To exclude the possibility that monoubiquination of H4 lysine 31 also affects ATM activation, Cul4A and DDB1 were depleted in cells. Depletion of Cul4A and DDB1 did not affect ATM autophosphorylation (FIG. 3c-d), suggesting ATM activation is independent of hisuutone H4 K31 monoubiquitination.

Figure 4H:
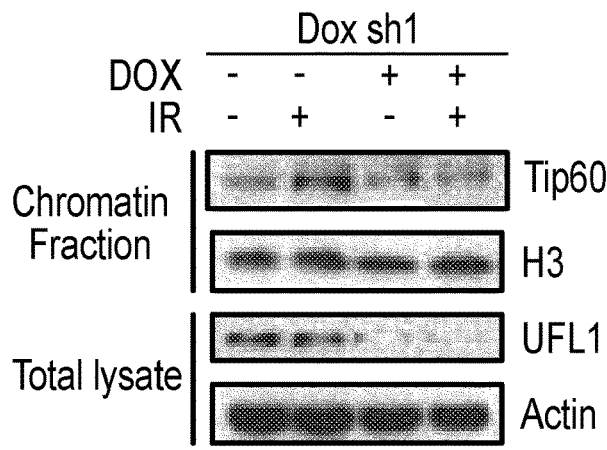
Figure 4I:
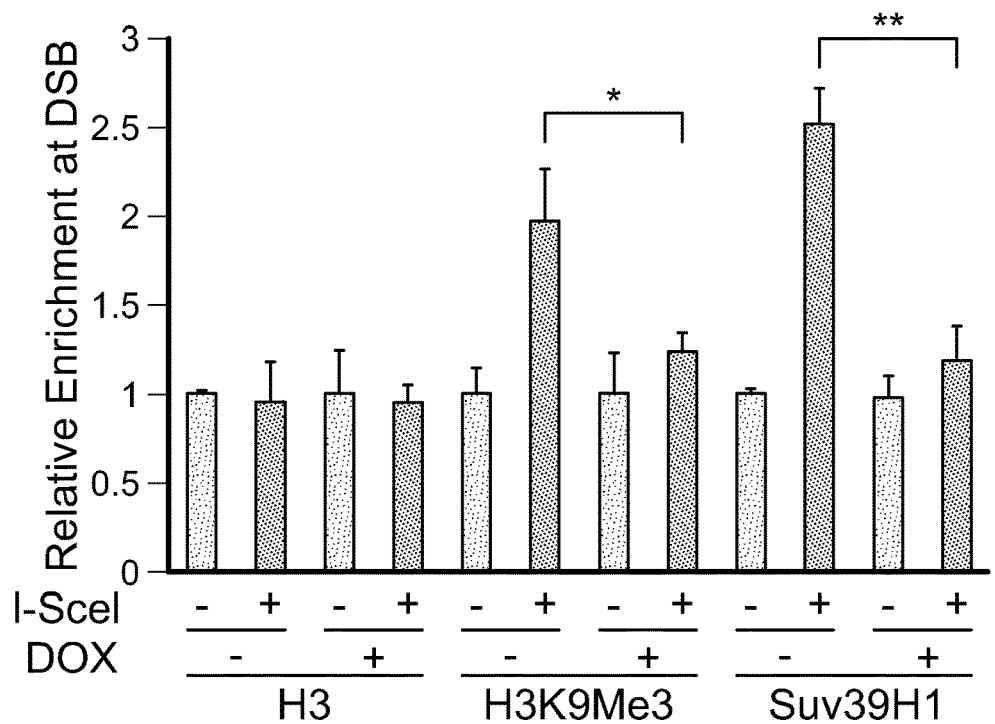
Figure 4J:
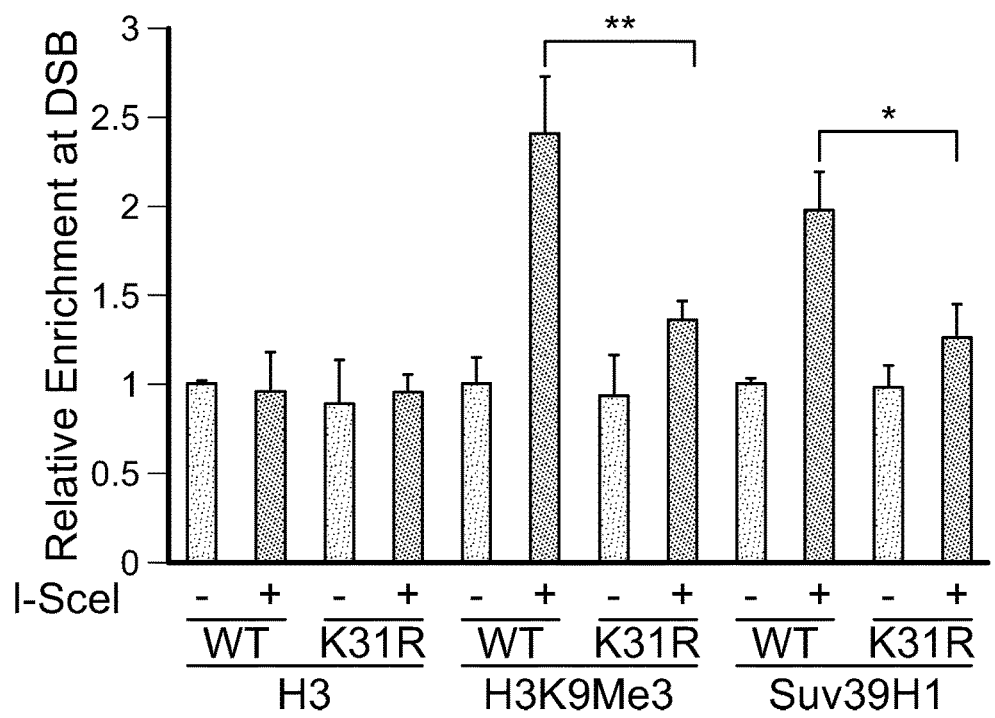

How UFL1-mediated histone H4 ufmylation affected ATM activation was studied. Depletion of UFL1 led to less Tip60 loaded to chromatin (FIG. 4h). These results implied that UFL1 regulated ATM activation through Tip60. As Tip60 recruitment to DSBs requires histone H3K9me3, the ability of UFL1 to regulate H3K9me3 was examined. A system in which expression of exogenous I-SceI introduced a single DSB in the genome (Moynahan et al., *Mol. Cell,* 7:263-272 (2001)) was used. Following I-SceI induced DSBs, ChIP assays were performed using antibodies against Suv39h1, H3K9Me3, and H3 and followed by qPCR to determine the relative abundance of these modifications at the induced break sites. Consistent with previous results (Ayrapetov et al., *Proc. Natl. Acad. Sci. USA,* 111:9169-9174 (2014)), an apparent increase of Suv39h1 and H3K9Me3 around DSBs was observed (FIG. 4i). Additionally, UFL1-depletion inhibited the accumulation of Suv39h1 and H3K9Me3 around DSBs (FIG. 4i). Furthermore, overexpression of histone H4K31R also resulted in decreased Suv39h1 and H3K9Me3 around DSBs (FIG. 4j). These results suggest that UFL1-mediated histone H4 ufmylation is important for the recruitment of Suv39h1, histone H3K9 methylation at DSB sites, and subsequent Tip60 recruitment and ATM activation.

Figure 5F:
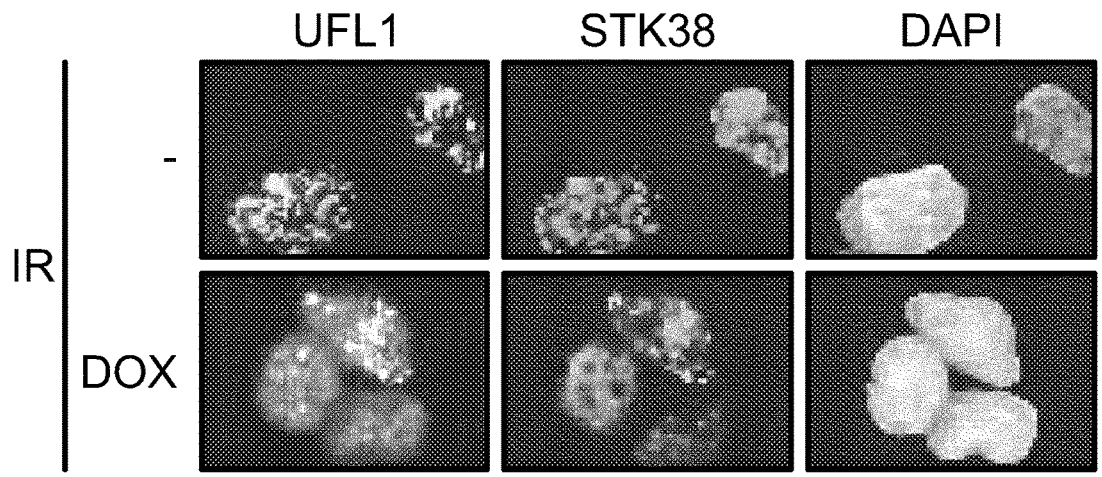
FIG. 5. STK38 recognizes H4 ufmylation and enhances ATM activation. a, List of UFM1-H4 and Ub-H4 interacting partners identified by mass spectrometric analysis. b, Purified His-UFM1-H4 or His-Ub-H4 interacts with GST-STK38 protein in vitro. c, Coimmunoprecipitation of UFM1-H4 protein with the Suv39h1-Kap1-HP1 complex. d, Coimmunoprecipitation of UFM1-H4 protein with the Suv39h1-Kap1-HP1 complex with or without knockdown of STK38. e, Immunofluorescence of STK38 after IR (2 Gy). f, Immunofluorescence of STK38 in UFL1-depleted cells. g, ATM signaling in STK38 depleted U2OS cells after IR. h, ATM signaling in STK38-depleted cells or cells reconstituted with HA-STK38. i, Analysis of H3K9 trimethylation (H3K9Me3) and Suv39h1 recruitment at DSB sites by ChIP from MDA-MB-231 ROS8 cells after the indicated treatment.
Figure 6D:
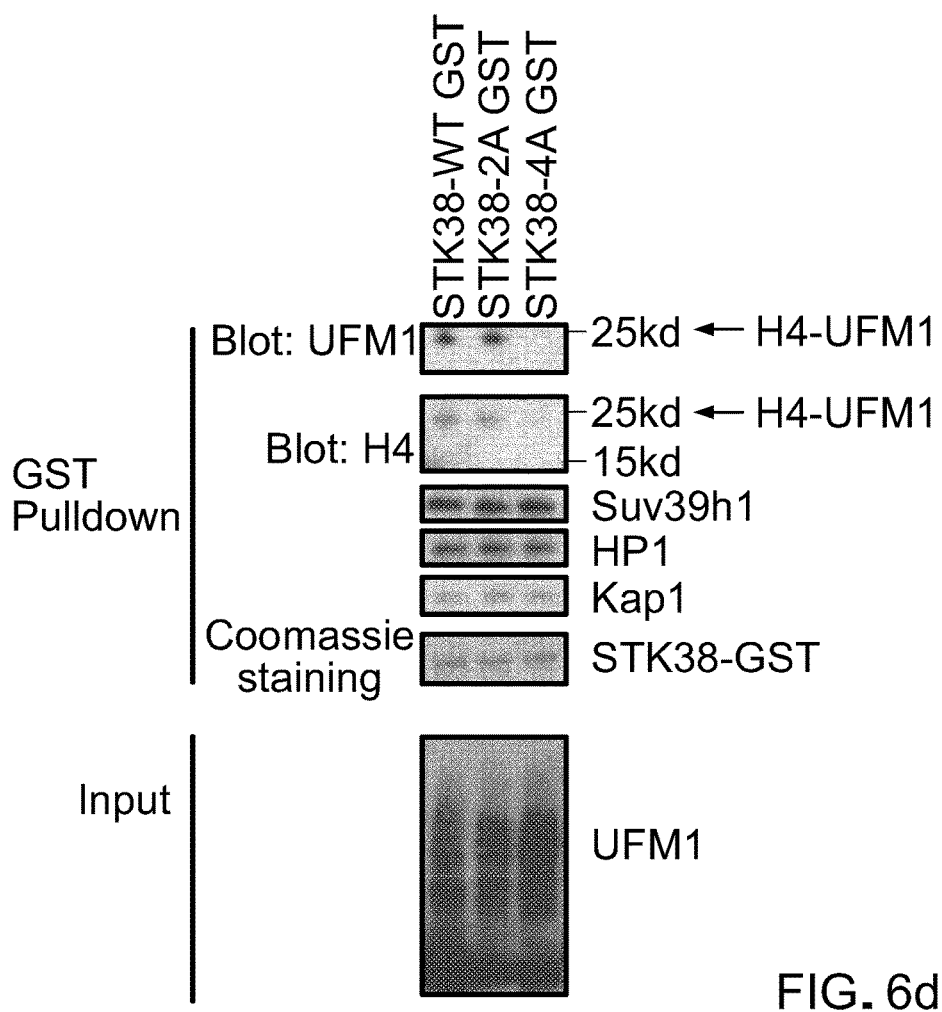
FIG. 6. STK38 is a reader of histone 4 ufmylation. a, STK38 interacts with the Suv39h1-KAP1-HP1α complex. Co-immunoprecipitation of STK38 and Suv39h1-KAP1-HP1α complex in U2OS cells. b, Purified GST or GST-STK38 protein incubated with irradiated U2OS cells lysates for 1 h and then blotted with the indicated antibodies. c, Analysis of UFM1 binding motif in STK38 sequence. d, Purified wildtype (WT) GST-STK38 and mutants proteins were incubated with irradiated U2OS cells lysates for 1 h and then blotted with the indicated antibodies. e, Immunofluorescence of STK38 and γ H2AX in irradiated cells expressing WT STK38 and mutant STK38 lacking kinase activity (K118R). f, ATM signaling in STK38-depleted cells reconstituted with WT or K118R mutant STK38.

It is unclear how increased histone H4 ufmylation following DNA damage is connected to H3K9me3. A search for potential histone H4 ufmylation readers was performed. UFM1-H4 and Ubquitin-H4 fusion constructs were constructed and utilized to pull down their interacting proteins, which were analyzed by mass spectrometry. STK38 was one of the top hits of UFM1-H4 interacting proteins, but was not identified among the Ubiquitin-H4 interacting proteins (FIG. 5a). This interaction was further confirmed by an in vitro binding assay (FIG. 5b), suggesting a direct interaction between STK38 and UFM1-H4. STK38 (serine/threonine kinase 38), also named as NDR1, is a member of the AGC kinase family (Hergovich et al., *Nat. Rev. Mol. Cell Biol.,* 7:253-264 (2006)). STK38 was reported to interact with HP1 (Chakraborty et al., *Nat. Commun.,* 5:3445 (2014)), which forms a complex with Kap-1, and Suv39h1 and helps promote H3K9 trimethylation (Ayrapetov et al., *Proc. Natl. Acad. Sci. USA*, 111:9169-9174 (2014)). Next, an immunoprecipitation assay was performed with STK38 antibody. STK38 interacted not only with HP1, but also with Kap-1 and Suv39h1 (FIG. 6a). From this, it was hypothesized that STK38 might be the link between histone H4 ufmylation and Suv39h1. Indeed, UFM1-H4 was able to pull down STK38, Kap-1, Suv39h1, and HP1 (FIG. 5c), and depletion of STK38 reduced these interactions (FIG. 5d). To further confirm this, a pulldown assay was performed, and STK38 protein was found to interact with ufmylated H4 (FIG. 6b). To explore how STK38 binds to ufmylated H4, STK38 protein sequence was analyzed, and a potential UFM1 binding motif, which is similar to UFM1 binding motif in UBA5 protein (Habisov et al., *J. Biol. Chem.*, 291:9025-9041 (2016)), was identified (FIG. 6c). Mutation of four critical amino acids to alanine abolished the interaction between STK38 and ufmylated H4 (FIG. 6d), without affecting the interaction between STK38 and HP1/Kap1/Suv39h1. Therefore, STK38 might be the H4K31 ufmylation reader and facilitate the accumulation of HP1/Kap-1/Suv39h1 complex to the DSBs, further promoting ATM activation.

Figure 5G:
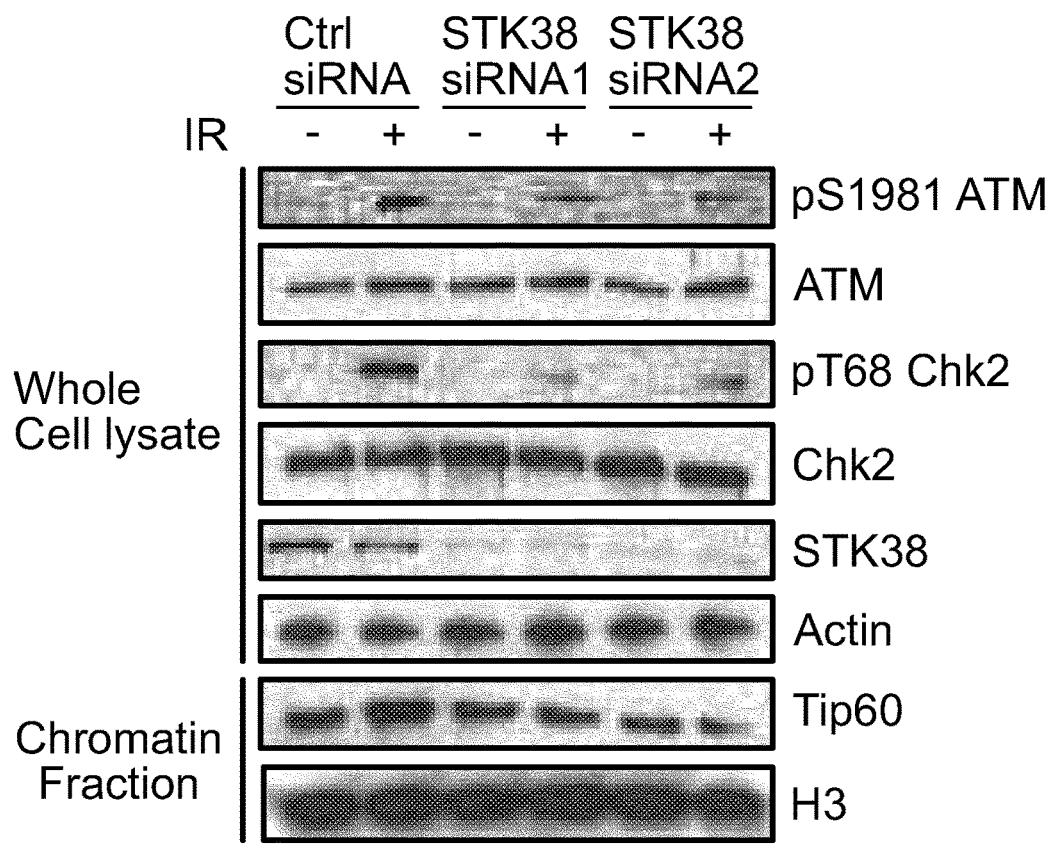
Figure 5H:
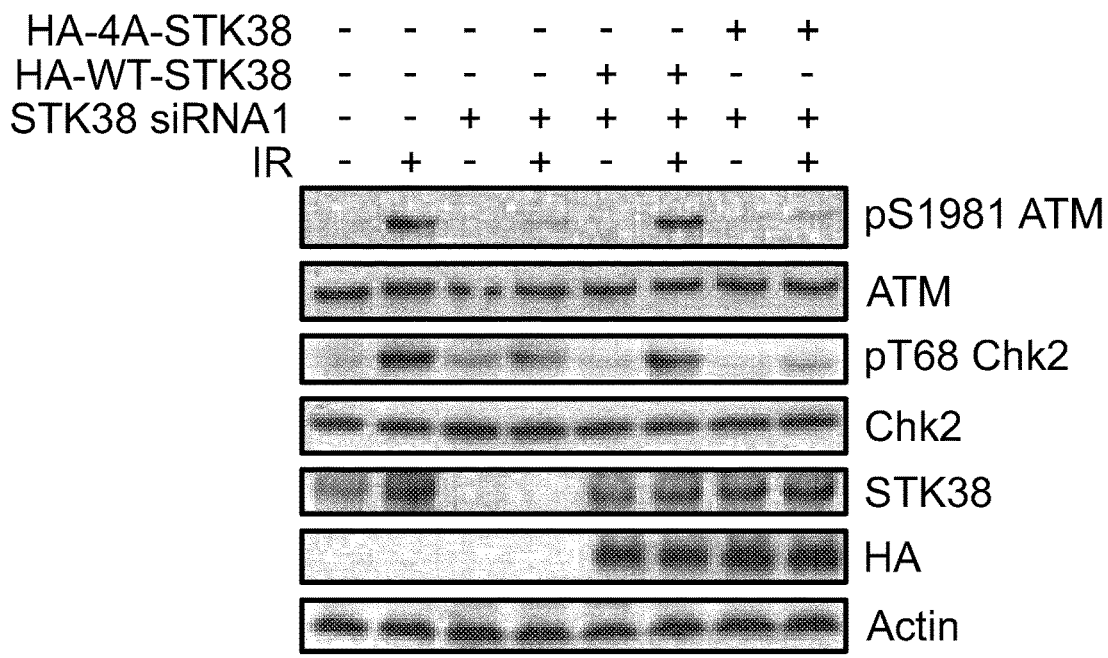
Figure 5I:
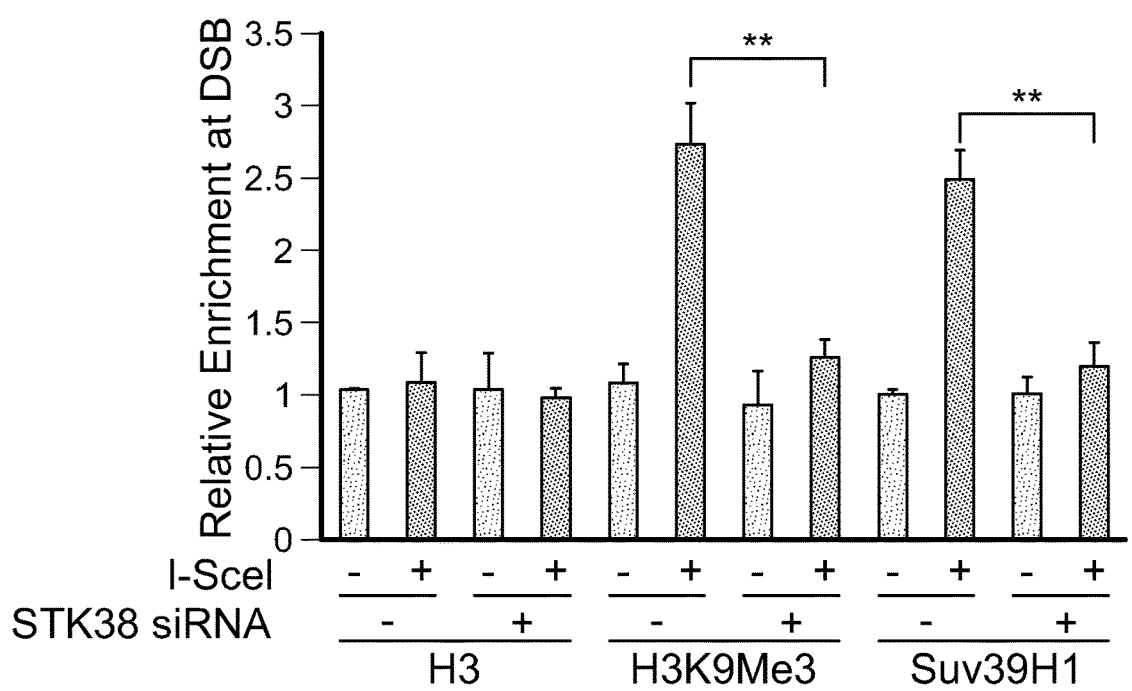
Figure 6E:
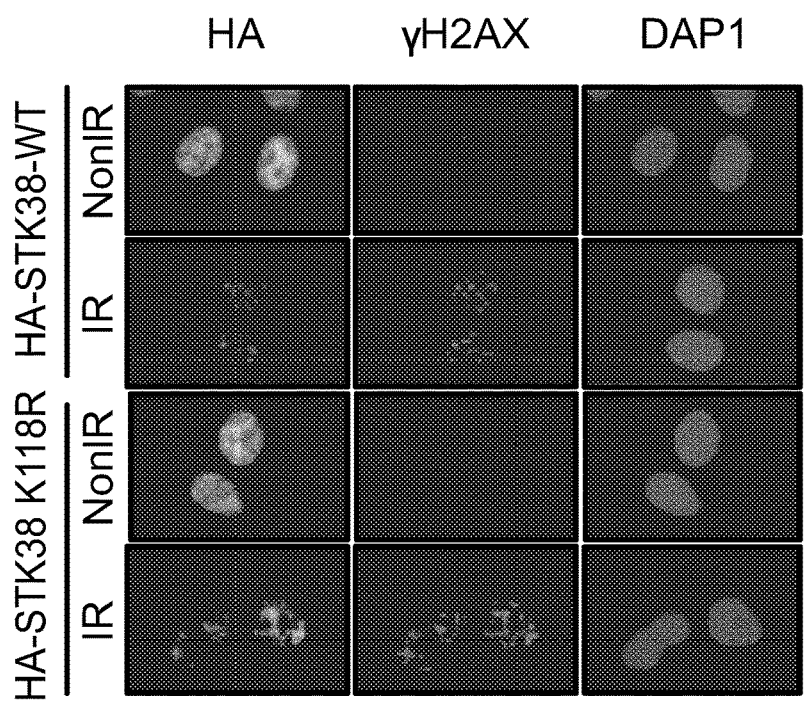
Figure 6F:
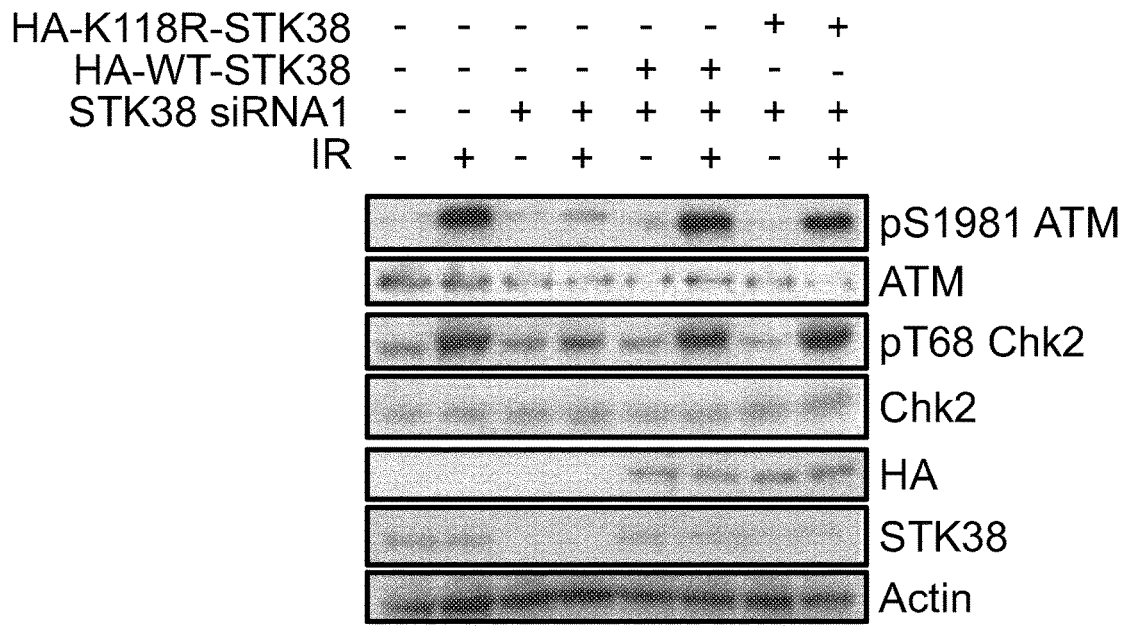

To test this hypothesis, whether STK38 was recruited to the DSBs was examined. STK38 was diffused in the nucleus without any stimuli, but gathered at DNA damage foci following DNA damage (FIG. 5e). Although it was a serine/threonine kinase, its kinase activity was not essential for its foci formation and ATM activation (FIG. 6e-f), and lack of UFL1 attenuated STK38 foci formation (FIG. 5f), suggesting ufmylation is important for STK38 recruitment to DNA lesions. To examine the effect of STK38 on ATM activation, STK38 was depleted in the cells. Depletion of STK38 impaired recruitment of Tip60 to chromatin and impeded ATM activation and its downstream signaling (FIG. 5g). Reconstitution of WT STK38, but not the STK38 4A mutant, rescued ATM activation in STK38 depleted cells (FIG. 5h). To further confirm this hypothesis, a ChIP assay was performed with Suv39h1, H3K9me3 and H3 antibodies. Loss of STK38 attenuated recruitment of Suv39h1 to DSBs and suppressed H3K9me3 modification at damage sites (FIG. 5i). Taken together, these results suggest that STK38 is a H4 ufmylation reader and facilitates the recruitment of the Suv39h1 to DSBs and ATM activation.

Figure 7A:
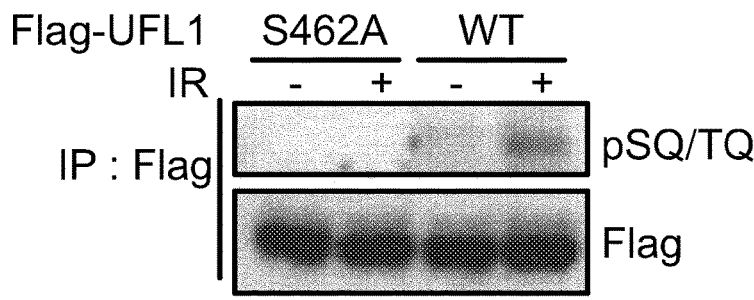
FIG. 7. ATM phosphorylates UFL1 at S462, and enhances its activity. a, Phosphorylation of wildtype (WT) Flag-UFL1 and S462A Flag-UFL1 mutant were analyzed with anti-pSQ/TQ antibody. b, In vitro ufmylation assay with Flag-UFL1 and its derivatives. c, His-Ufmylated H4 protein purified from ATM$^{+/+}$ and ATM$^{-/-}$ cells. d, ATM signaling in UFL1 shRNA expressing cells with reconstitution of Flag-UFL1 and its derivatives.
Figure 7B:
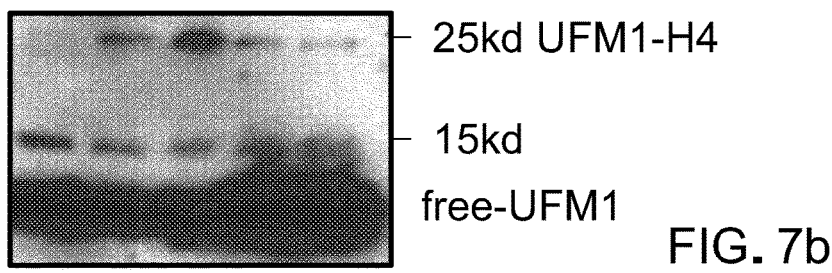

Increased histone H4 ufmylation following DNA damage suggests that UFL1 activity might be regulated, however, the mechanism how UFL1 activity is regulated following DNA damage is unknown. Interestingly, UFL1 was found to be phosphorylated at SQ/TQ motifs in an ATM-dependent manner (FIG. 7a-b), when an antibody against phospho-SQ/TQ motifs (Kim et al., *J. Biol. Chem.*, 274:37538-37543 (1999)) was used. These results suggest that UFL1 might be a substrate of ATM.

Figure 7C:
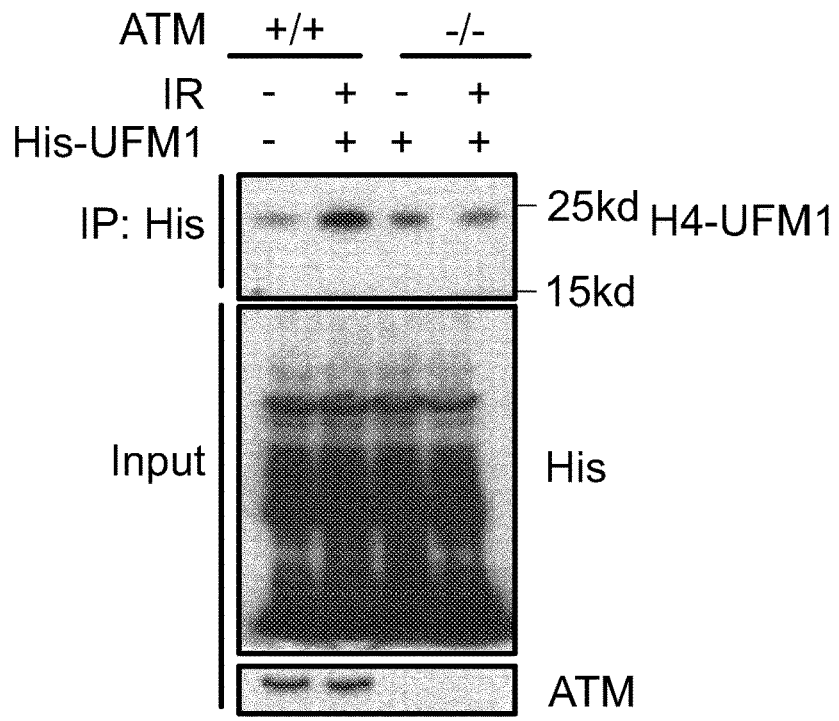
Figure 7D:
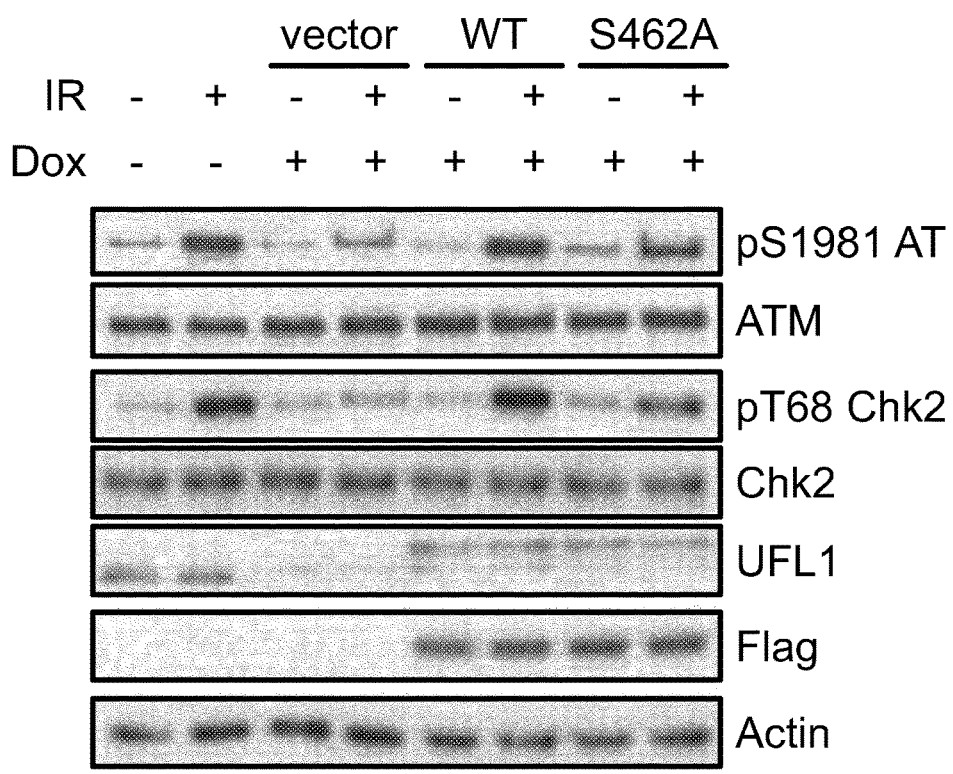

The following was performed to determine which sites of UFL1 are potentially phosphorylated by ATM. Among potential SQ/TQ sites, mutation of serine 462 to alanine abolished pSQ/TQ signals (FIG. 7a), suggesting that UFL1 S462 is a major ATM phosphorylation site. How UFL1 phosphorylation affected its function was assessed. Considering that phosphorylation can change enzymatic activity, it was hypothesized that UFL1 activity is changed by this phosphorylation. Purified WT UFL1 from cell lysate displayed increased E3 ligase activity following DNA damage, while the S462A mutant did not (FIG. 7b), suggesting that S462 phosphorylation is important for UFL1 activation following DNA damage. To further confirm this, ufmylated histone H4 was examined in control and ATM knockout MEF cells. Histone H4 ufmylation was increased in WT MEFs, but no change of histone H4 ufmylation was observed in ATM knockout cells (FIG. 7c), suggesting that the UFL1 ufmylation activity is dependent on intact ATM protein. Therefore, ATM and UFL1 form a positive feedback loop and promote activation of each other. In agreement, ATM activation and Chk2 phosphorylation were compromised in UFL1-deficient cells reconstituted with the UFL1 S462A (FIG. 7d).

Figure 8A:
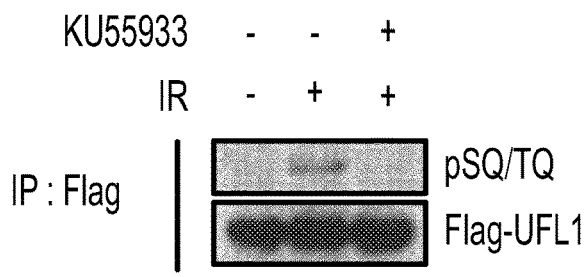
FIG. 8. ATM phosphorylates UFL1 at S462, and enhances its activity. a, Flag-UFL1 phosphorylation was analyzed with anti-pSQ/TQ antibody in the presence or absence of ATM inhibitor KU55933. b, UFL1 phosphorylation was examined in ATM+/+ or ATM−/− MEFs after IR. c, Working model: When DNA damage occurs, UFL1 is recruited by the MRN complex and monoufmylates histone H4. STK38 recognizes H4K31 monoufmylation, and recruits Suv39h1 to DSBs to trimethylates H3K9. Tip60 binds to H3K9me3 and acetylates ATM promoting ATM autophosphorylation and activation. C-Abl also phosphorylates Tip60 and enhances Tip60 acetyltransferase activity. Activated ATM phosphorylates UFL1 at Ser462, and enhances its activity to further amplify ATM activation signal in a positive feedback loop.
Figure 8B:
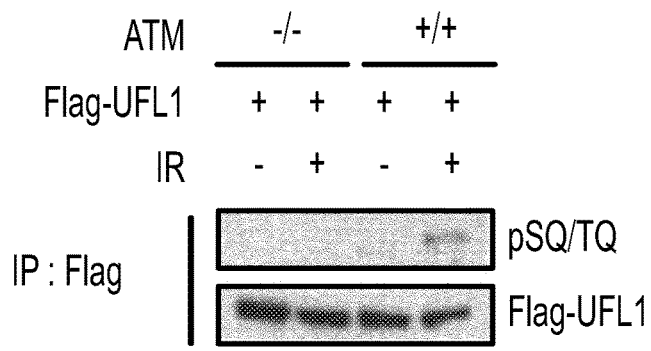
Figure 8C:
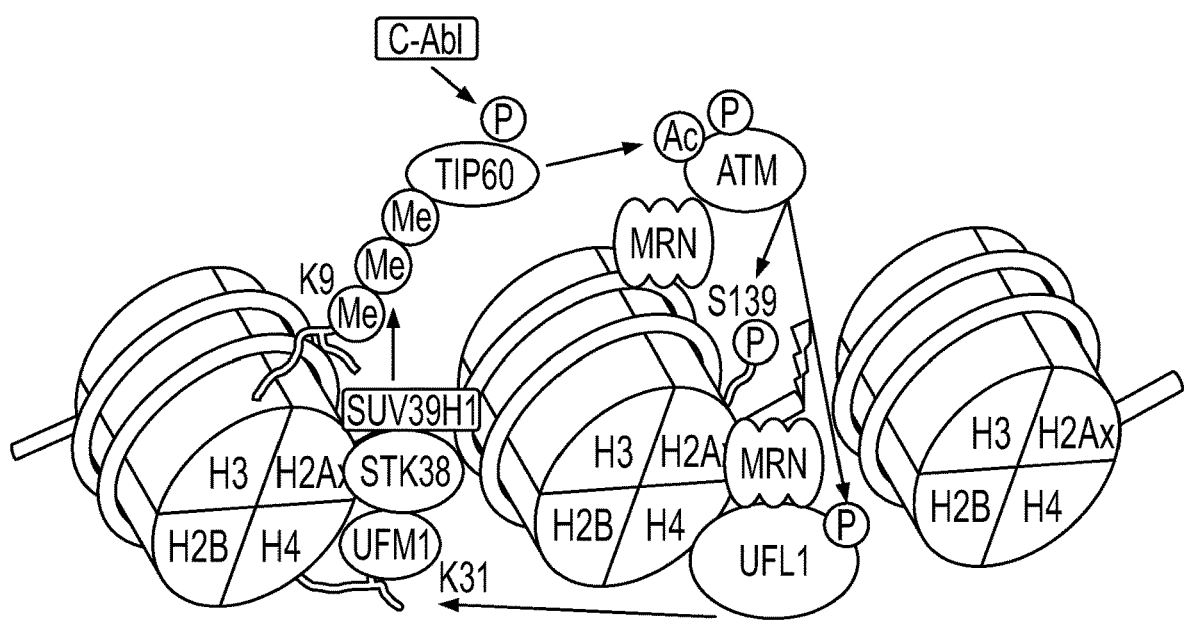
Figure 9:
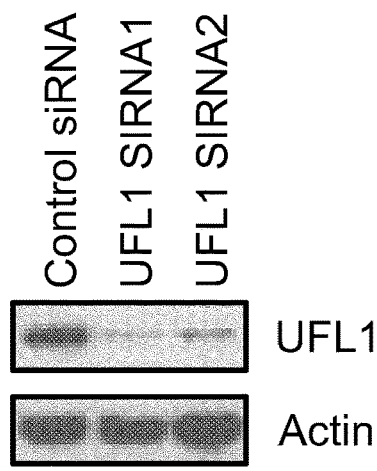
FIG. 9. U2OS cells were transfected with control siRNA and UFL1 siRNA1 and siRNA2. 48 hours later, cell were lysed, and analyzed by western blot with the indicated antibodies.

In summary, a new mechanism for ATM activation and the early DDR signaling was identified. Ufmylation-ubiquitin like protein modification was involved in DDR and DNA repair. These results indicate that UFL1 functions as a new ATM signaling regulator. As a UFM1 E3 ligase, UFL1 is recruited to chromatin via the MRN complex, and modifies histone H4 at K31. Ufmylated histone H4K31 is recognized by STK38, which is important for the recruitment of Suv39h1 to DSBs, histone H3 lysine9 trimethylation, Tip60 recruitment, and subsequent ATM activation. UFL1 itself is phosphorylated at S462 by ATM, which boosts its E3 ligase activity, forming a positive feedback loop to amplify ATM activation (FIG. 8c). These results demonstrate that inhibiting UFM1 activity or expression and/or UFL1 activity or expression reduce DDR and DNA repair in cells such as cancer cells, thereby making those cells susceptible to DNA damaging therapies such as radiation and chemotherapy.

Example 2—Increasing the Sensitivity of Cancer Cells to Treatment with Ionizing Radiation Cell Culture and Antibodies U2OS cells were cultured in DMEM supplemented with 10% FBS. Cells were kept in a humidified 37° C. (5% $CO_2$ 5% $O_2$) incubator.

Anti-actin antibodies were obtained from Sigma. Anti-ATM, anti-pSer1981 ATM, anti-Chk2, and anti-phospho-Chk2 antibodies were obtained from Cell Signaling. Anti-UFM1 antibodies were obtained from Santa Cruz.

UFL1 Inhibition

U2OS cells were plated in 6 well plates, and MEK1 inhibitors (AZD6244 or GDC0623) were added to wells with 10 μM final concentration and incubated for 48 hours. AZD6244 was purchased from Selleckchem. In some cases, cells were also irradiated with IR (10 Gy IR for 30 minutes).

Western Blot

Cells were washed once with PBS and lysed with SDS lysis buffer. The samples were separated by SDS-PAGE following three washes with NETN buffer. Western blots were carried out following standard procedures.

Results

To identify an inhibitor of UFL1 activity that induced a significant decrease of ufmylation, cells were treated with inhibitors and were analyzed by western blot using UFM1 antibody to detect the ufmylation level in the cells.

Figure 10:
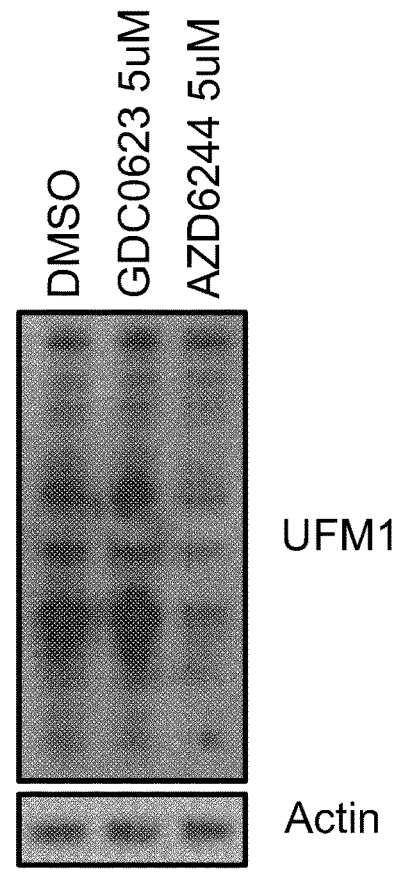
FIG. 10. U2OS cells were treated with AZD6244 or GDC0623. 48 hours later, cell were harvested, lysed, and analyzed by western blot with the indicated antibodies.

U2OS cells were treated with two different MEK1 inhibitors (AZD6244 or GDC0623). With AZD6244 treatment, the ufmylation level in the cells were greatly suppressed (FIG. 10).

Figure 11:
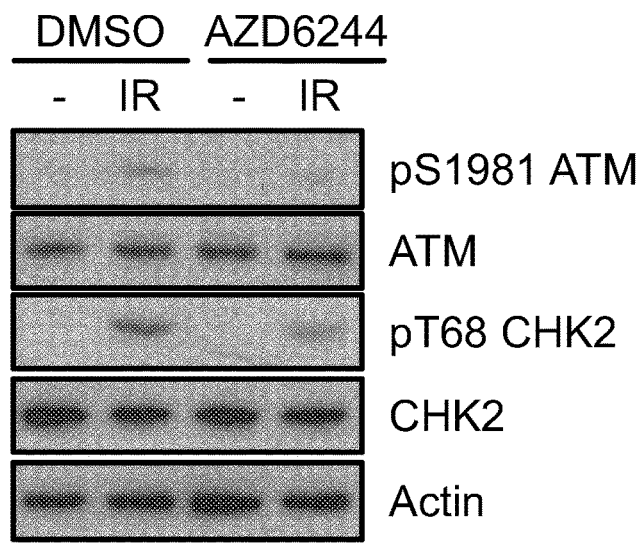
FIG. 11. U2OS cells were pretreated with AZD6244. 6 hours later, cells were treated with 10 Gy IR. 30 minutes after ionizing radiation, cells were harvested, lysed, and analyzed by western blot with the indicated antibodies.

U2OS cells were pretreated with AZD6244, and then irradiated with IR. Protein kinase ataxia-telangiectasia mutated (ATM) signaling was greatly suppressed with AZD6244 treatment (FIG. 11).

These results demonstrate that AZD6244 inhibits UFL1.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer in a mammal, wherein said method comprises:
   (a) administering AZD6244 to said mammal, and
   (b) administering a DNA damaging therapy to said mammal,
   wherein the number of cancer cells within said mammal is reduced to a greater level than the level observed in a comparable mammal administered said DNA damaging therapy in the absence of administration of said AZD6244.

2. The method of claim 1, wherein said mammal is a human.

3. The method of claim 1, wherein said cancer is prostate cancer.

4. The method of claim 1, wherein said cancer is breast cancer.

5. The method of claim 1, wherein said cancer is resistant to radiation when administered as the sole cancer therapy.

6. The method of claim 1, wherein said DNA damaging therapy is radiation therapy.

7. A method for treating cancer in a mammal, wherein said method comprises:

(a) administering nucleic acid designed to promote RNA interference of UFL1 polypeptide expression to said mammal, and
(b) administering a DNA damaging therapy to said mammal,
wherein the number of cancer cells within said mammal is reduced to a greater level than the level observed in a comparable mammal administered said DNA damaging therapy in the absence of administration of said nucleic acid designed to promote RNA interference of UFL1 polypeptide expression.

8. The method of claim 7, wherein said mammal is a human.

9. The method of claim 7, wherein said nucleic acid designed to promote RNA interference of UFL1 polypeptide expression comprises nucleic acid encoding an shRNA targeting UFL1.

10. The method of claim 9, wherein said nucleic acid encoding said shRNA targeting UFL1 is selected from the group consisting of GAAACACTTCTGTGTCAGAAA (SEQ ID NO:1), GCTCTGGAACATGGGTTGATA (SEQ ID NO:2), CCAGTAAGCATAAGTCATATT (SEQ ID NO:22), and GAGAGAGAACACATGCAATTT (SEQ ID NO:23).

11. The method of claim 7, wherein said nucleic acid designed to promote RNA interference of UFL1 polypeptide expression is an siRNA targeting UFL1.

12. The method of claim 11, wherein said siRNA targeting UFL1 is selected from the group consisting of CAGAAGAGGUCAAUGAUAAUU (SEQ ID NO:24), UCAUAUGGGCAAAGGGAAAUU (SEQ ID NO:25), CAGAAGAGGUCAAUGAUAA (SEQ ID NO:26), and UCAUAUGGGCAAAGGGAAA (SEQ ID NO:27).

13. The method of claim 7, wherein said cancer is prostate cancer.

14. The method of claim 7, wherein said cancer is breast cancer.

15. The method of claim 7, wherein said cancer is resistant to radiation when administered as the sole cancer therapy.

16. The method of claim 7, wherein said DNA damaging therapy is radiation therapy.

* * * * *